(12) United States Patent
Henao et al.

(10) Patent No.: US 9,399,605 B2
(45) Date of Patent: Jul. 26, 2016

(54) OXYGEN STORAGE AND CATALYTIC ALKANE CONVERSION

(71) Applicant: ExxonMobil Chemical Patents Inc., Baytown, TX (US)

(72) Inventors: Juan D. Henao, Houston, TX (US); Paul F. Keusenkothen, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 152 days.

(21) Appl. No.: 14/469,180

(22) Filed: Aug. 26, 2014

(65) Prior Publication Data

US 2015/0065773 A1 Mar. 5, 2015

Related U.S. Application Data

(60) Provisional application No. 61/872,175, filed on Aug. 30, 2013.

(30) Foreign Application Priority Data

Oct. 22, 2013 (EP) ..................................... 13189746

(51) Int. Cl.
*C07C 5/327* (2006.01)
*C07C 5/333* (2006.01)
(Continued)

(52) U.S. Cl.
CPC ................. *C07C 2/84* (2013.01); *B01J 8/0207* (2013.01); *B01J 15/005* (2013.01); *B01J 19/24* (2013.01); *B01J 19/245* (2013.01); *C07C 2/08* (2013.01);
(Continued)

(58) Field of Classification Search
CPC ............ C07C 5/327; C07C 5/333; C07C 7/12
USPC .......................... 585/943, 654, 656, 658, 820
See application file for complete search history.

(56) References Cited

U.S. PATENT DOCUMENTS 3,435,089 A 3/1969 Moore, Jr. et al.
4,144,277 A 3/1979 Walker et al.
(Continued)

FOREIGN PATENT DOCUMENTS

DE 275 452 1/1990
FR 1 588 738 4/1970
(Continued)

OTHER PUBLICATIONS

Bloch et al., "*Hydrocarbon Separations in a Metal Organic Framework with Open Iron(II) Coordination Sites,*" Science, vol. 335, pp. 1606-1610, 2012.
(Continued)

*Primary Examiner* — Thuan D Dang

(57) ABSTRACT

The inventing relates to hydrocarbon conversion, and more particularly to catalytically converting alkane in the presence of oxygen released from an oxygen storage material. Conversion products include $C_2$ hydrocarbon, such as $C_{2+}$ olefin. The hydrocarbon conversion process can be an oxidative coupling reaction, which refers to the catalytic conversion of methane in the presence of oxidant to produce the olefin product. Flow-through reactors can be used to carry out oxygen storage and the oxidative coupling reaction. Reverse-flow reactors are examples of flow-through reactors, which can be used to carry out oxygen storage and the oxidative coupling reaction.

12 Claims, 4 Drawing Sheets

(51) Int. Cl.

| | | |
|---|---|---|
| C07C 7/12 | (2006.01) | |
| C07C 2/84 | (2006.01) | |
| B01J 8/02 | (2006.01) | |
| C07C 2/42 | (2006.01) | |
| B01J 19/24 | (2006.01) | |
| C07C 2/08 | (2006.01) | |
| C07C 5/48 | (2006.01) | |
| C07C 7/00 | (2006.01) | |
| B01J 15/00 | (2006.01) | |
| C07C 2/78 | (2006.01) | |
| B01D 53/04 | (2006.01) | |

(52) U.S. Cl.
CPC ..... C07C 2/42 (2013.01); C07C 2/78 (2013.01); C07C 5/48 (2013.01); C07C 7/005 (2013.01); C07C 7/12 (2013.01); B01D 53/04 (2013.01); B01D 2256/24 (2013.01); B01D 2257/7022 (2013.01); B01D 2259/4009 (2013.01); B01J 2208/0053 (2013.01); B01J 2208/00309 (2013.01); B01J 2208/00548 (2013.01); B01J 2208/00557 (2013.01); B01J 2208/00566 (2013.01); B01J 2219/24 (2013.01); B01J 2219/2402 (2013.01); Y02P 20/51 (2015.11)

(56) References Cited

U.S. PATENT DOCUMENTS

| | | | |
|---|---|---|---|
| 4,751,336 | A | 6/1988 | Jezl et al. |
| 4,754,093 | A | 6/1988 | Jezl et al. |
| 4,754,095 | A | 6/1988 | Coughenour et al. |
| 4,988,660 | A * | 1/1991 | Campbell ............... B01J 23/002 502/302 |
| 5,095,161 | A | 3/1992 | Abrevaya et al. |
| 5,336,825 | A | 8/1994 | Choudhary et al. |
| 5,936,135 | A | 8/1999 | Choudhary et al. |
| 6,258,993 | B1 | 7/2001 | Carr et al. |
| 7,022,888 | B2 | 4/2006 | Choudhary et al. |
| 2002/0020113 | A1 | 2/2002 | Kennedy et al. |
| 2009/0292153 | A1 | 11/2009 | Cai et al. |
| 2010/0290978 | A1 | 11/2010 | Chun et al. |
| 2011/0315012 | A1 | 12/2011 | Kuznicki et al. |
| 2011/0320176 | A1 | 12/2011 | Haldoupis et al. |
| 2014/0018589 | A1 | 1/2014 | Iyer et al. |
| 2015/0065767 | A1 | 3/2015 | Henao et al. |
| 2015/0065769 | A1 | 3/2015 | Henao et al. |
| 2015/0065771 | A1 | 3/2015 | Keusenkothen |

FOREIGN PATENT DOCUMENTS

| | | |
|---|---|---|
| GB | 855 764 | 12/1960 |
| WO | WO 91/04240 | 4/1991 |
| WO | WO 95/20556 | 8/1995 |
| WO | WO 02/24614 | 3/2002 |
| WO | WO 2007/075945 | 7/2007 |
| WO | WO 2011/149996 | 12/2011 |

OTHER PUBLICATIONS

Centi et al., "Direct Conversion of Methane, Ethane and Carbon Dioxide to Fuels and Chemicals," The Catalyst Group Resources Inc., Spring House, 2008.
Choudhary et al., "Low-Temperature Nonoxidative Activation of Methane over H-Galloaluminosilicate (MFI) Zeolite," Science, vol. 275, pp. 1286-1288, 1997.
Choudhary et al., "Product Selectivity and Aromatics Distribution in Aromatization of Propane Over H-GaMFI Zeolite: Influence of Temperature," Microporous and Mesoporous Materials, vol. 23, Issues 3-4, pp. 231-238, 1998.
Das et al., "Interplay of Metalloligand and Organic Ligand to Tune Micropores within Isostructural Mixed-Metal Organic Frameworks (M'MOFs) for Their Highly Selective Separation of Chiral and Achiral Small Molecules," Journal of the American Chemical Society, vol. 134, Issue 20, pp. 8703-8710, 2012.
Gucuyener et al., "Ethane/Ethene Separation Turned on Its Head: Selective Ethane Adsorption on the Metal-Organic Framework ZIF-7 through a Gate-Opening Mechanism," Journal of the American Chemical Society, vol. 132, Issue 50, pp. 17704-17706, 2010.
Guo et al., "Dehydrogenation and Aromatization of Propane over Rhenium-Modified HZSM-5 Catalyst," Journal of Molecular Catalysis A: Chemical, vol. 239, Issue 1-2, pp. 222-227, 2005.
Guo et al., "Energy Efficient Coaromatization of Methane and Propane," Journal of Natural Gas Chemistry, vol. 18, Issue 3, pp. 260-272, 2009.
He et al., "High Separation Capacity and Selectivity of $C_2$ Hydrocarbons over Methane with a Microporous Metal-Organic Framework at Room Temperature," Chemistry—A European Journal, vol. 18, Issue 7, pp. 1901-1904, 2012.
Liu et al., "Scale Up and Stability Test for Oxidative Coupling of Methane Over $Na_2$ $WO_4$-$Mn/SiO_2$ Catalyst in a 200 ml Fixed-Bed Reactor," Journal of Natural Gas Chemistry, vol. 17, No. 1, pp. 59-63, Mar. 2008.
Tonkovich et al., "A Simulated Countercurrent Moving-Bed Chromatographic Reactor for the Oxidative Coupling of Methane: Experimental Results," Chemical Engineering Science, vol. 49, No. 24, pp. 4647-4656, 1994.
Aguado et al., "Absolute Molecular Sieve Separation of Ethylene/Ethane Mixtures with Silver Zeolite A," Journal of the American Chemical Society 2012, vol. 134, pp. 14635-14637.
Ghose et al., "Solution Combustion Synthesized Catalytic Materials for Oxidative Coupling of Methane," $23^{rd}$ North American Catalysis Society Meeting, Jun. 5, 2013. (Extended Abstract).
Jiang et al., "Methane to Ethylene with 85 Percent Yield in a Gas Recycle Electrocatalytic Reactor-Separator", Science, vol. 264, No. 5165, Jun. 10, 1994, pp. 1563-1566.
Keller et al., "Synthesis of Ethylene via Oxidative Coupling of Methane", Journal of Catalysis 73 (1982), pp. 9-19.
Korf et al., "The Development of Doped Li/MgO Catalyst Systems for the Low-Temperature Oxidative Coupling of Methane", Methane Conversion by Oxidative Processes—Fundamental and Engineering Aspects, Van Nostrand Reinhold / Springer, US, pp. 168-199. 1992.
Kruglov et al. "Optimization of the Simulated Countercurrent Moving-Bed Chromatographic Reactor for the Oxidative Coupling of Methane," Chemical Engineering Science, vol. 51, No. 11 (1996), pp. 2945-2950.
Liu et al., "Autothermal Reforming of Methane in a Reverse-Flow Reactor", Chemical Engineering & Technology, vol. 32, No. 9, Sep. 1, 2009, pp. 1358-1366.
Machocki et al., "Methane Oxidative Coupling in an Undiluted Reactor Mixture in a Reactor-Adsorber System With Gas Recirculation," Applied Catalysis A: General 146 (1996), pp. 391-400.
Mattisson, T., "Materials for Chemical-Looping with Oxygen Uncoupling," Hindawi Publishing Corporation, ISRN Chemical Engineering, vol. 2013, Article ID 526375, 19 pages.
Mehdipour et al., "Modeling of a PSA-TSA Process for Separation of $CH_4$ from $C_2$ Products of OcM Reaction," Separation Science and Technology, vol. 47, No. 8 (2012), pp. 1199-1212.
Mleczko et al., "Catalytic Oxidative Coupling of Methane—Reaction Engineering Aspects and Process Schemes," Fuel Processing Technology, Elsevier BV, NL, vol. 42, No. 2-3, Apr. 1, 1995, pp. 217-248.
Mortazavi et al., "Catalytic Methane Coupling Under Periodic Operation", The Canadian Journal of Chemical Engineering, vol. 74, No. 5, Oct. 1, 1996, pp. 683-694.
Olivier et al., "High-Temperature Parallel Screening of Catalysts for the Oxidative Coupling," Catalysis Today, vol. 137 (2008), pp. 80-89.
SRI, Ethylene from Methane, Process Economics Program Report No. 208 (Jan. 1994), 139 pages.
Tonkovich et al., "Enhanced C2 Yields from Methane Oxidative Coupling by Means of a Separative Chemical Reactor", Science, vol. 262, No. 5131, Oct. 8, 1993, pp. 221-223.

(56) References Cited

OTHER PUBLICATIONS

Veser et al., "*Multiscale Process Intensification for Catalytic Partial Oxidation of Methane: From Nanostructured Catalysts to Integrated Reactor Concepts*", Catalysis Today, Elsevier, NL, vol. 157, No. 1-4, Nov. 17, 2010, pp. 24-32.

Yentekakis et al., "*Oxidative Coupling of Methane to Ethylene with 85% Yield in a Gas Recycle Electrocatalytic Reactor Separator*," Studies in Surface Science and Catalysis, vol. 107 (1997), pp. 307-312.

Farsi et al., "Kinetics investigation of direct natural gas conversion by oxidative coupling of methane", Journal of Natural Gas Science and Engineering, 2(2010), 270-274.

\* cited by examiner

OXYGEN STORAGE AND CATALYTIC ALKANE CONVERSION

CROSS-REFERENCE TO RELATED APPLICATION

This application claims priority to and the benefit of (i) U.S. Provisional Patent Application No. 61/872,175, filed Aug. 30, 2013; (ii) E.P. Patent Application No. 13189746.4, filed Oct. 22, 2013; and (iii) U.S. Provisional Patent Application No. 61/912,901, filed Dec. 6, 2013; the contents of which are incorporated herein by reference in their entireties. The following related cases are also incorporated by reference in their entireties: (i) P.C.T. Patent Application No. PCT/US2014/052698, filed Aug. 26, 2014; (ii) U.S. patent application Ser. No. 14/469,109, filed Aug. 26, 2014; (iii) P.C.T. Patent Application No. PCT/US2014/052710, filed Aug. 26, 2014; (iv) U.S. patent application Ser. No. 14/469,141, filed Aug. 26, 2014; (v) P.C.T. Patent Application No. PCT/US2014/052722, filed Aug. 26, 2014; (vi) U.S. patent application Ser. No. 14/469,227, filed Aug. 26, 2014; and (vii) P.C.T. Patent Application No. PCT/US2014/052715, filed Aug. 26, 2014.

FIELD OF THE INVENTION

The invention relates to processes for catalytically converting alkane. The invention further relates to processes for oxygen storage and catalytically converting alkane to produce $C_{2+}$ unsaturates, and to equipment useful in such processes.

BACKGROUND OF THE INVENTION

Producing ethylene by methane dehydrogenation is an energy-intensive reaction. Since the reaction is endothermic and reaction temperatures greater than 800° C. are generally required to achieve practical methane conversion levels, a significant amount of heat is required to maintain the reaction. Generating this heat and transferring it to the methane is a significant cost and can introduce inefficiencies into the process. In order to overcome some of these difficulties, there has been considerable effort directed toward methane conversion via catalytic oxidative coupling reactions.

One process for producing ethylene from methane by catalytic oxidative coupling is disclosed in *Synthesis of Ethylene via Oxidative Coupling of Methane*, G. E. Keller and M. H. Bhasin, Journal of Catalysis 73, 9-19 (1982). Although an appreciable selectivity to ethylene was observed (to a maximum of about 50%), conversion was relatively low. In order to overcome the methane-ethylene separation difficulties resulting from the low methane conversion, technology has been developed for quenching the reaction product downstream of the oxidative coupling reactor, and then separating ethylene from the unreacted methane.

One process, disclosed in *Enhanced $C_2$ Yields from Methane Oxidative Coupling by Means of a Separative Chemical Reactor*, A. E. Tonkovich, R. W. Carr, R. Aris, Science 262, 221-223, 1993, includes a simulated countercurrent moving-bed chromatographic reactor, and achieves 65% methane conversion and 80% selectivity to $C_2$ hydrocarbons. The reactor is configured in four sections, with each section comprising (i) a catalytic reactor containing $Sm_2O_3$ catalyst and (ii) an adsorbent column located downstream of the catalytic reactor. Methane and oxygen react via catalytic oxidative coupling in the reactor at a temperature in the range of about 900° K to 1100° K, and then ethylene is separated from unreacted methane in the sorption column. In order to maintain sufficient selectivity for ethylene sorption, the reactor's product is quenched to a temperature of 373° K in the sorption column. In another process, disclosed in *Methane to Ethylene with 85 Percent Yield in a Gas Recycle Electrocatalytic Reactor-Separator*, Y. Jiang, I. V. Yentekakis, C. G. Vayenas, Science 264, 1563-1566, 1994, gas recycle is utilized to further increase methane conversion, but an even lower quench temperature (30° C.) is used during ethylene sorption.

Although the disclosed moving-bed and gas-recycle processes improve conversion, the quenching is energy-intensive, and further improvements are desired. Further improvements are particularly desired in converting alkanes such as methane into higher order hydrocarbon, e.g., into $C_{2+}$ olefins such as ethylene and propylene.

Improvements in distribution of oxygen for carrying out the conversion of alkane such as methane into higher order hydrocarbon, such as $C_{2+}$ olefin, are also desired. Additionally, reduction in undesired combustion reactions competing with the alkane conversion is desired.

SUMMARY OF THE INVENTION

Certain aspects of the invention provide a hydrocarbon conversion process that is less energy-intensive and has greater selectivity for the desired products than comparable processes. The hydrocarbon conversion process is particularly desirable for converting alkane such as methane into (i) higher order hydrocarbon (e.g., by alkane coupling) and/or (ii) unsaturated hydrocarbon, e.g., to olefin, such as ethylene and propylene. The unsaturated hydrocarbon can be produced from the alkane and/or coupled alkane. The process is advantageous, in part because the conversion exhibits increased selectivity for $C_{4-}$ olefin production and decreased selectivity for $CO_2$ production. The process further provides for efficient distribution of oxygen for carrying out the conversion of alkane such as methane into $C_{2+}$ olefins. Additionally, the process reduces undesired combustion reactions that would otherwise compete with the desired conversion reaction.

More particularly, the invention relates to a process for producing a $C_{2+}$ composition. The process includes a step of providing a flow-through reactor comprising (i) a hydrocarbon conversion catalyst having at least one of oxidative coupling functionality and oxydehydrogenation functionality and (ii) an oxygen storage material. The flow-through reactor typically comprises thermal mass, e.g., thermal mass associated with the hydrocarbon conversion catalyst and/or the oxygen storage material. The process can be carried out during distinct time intervals.

During a first time interval, oxidant is passed through the flow-through reactor system, and at least a portion of the oxidant's oxygen is transferred to and stored with the oxygen storage material. Oxygen is stored with the oxygen storage material, typically in, on, or within the oxygen storage material, or as part of the oxygen storage material's composition. The flow of oxidant through the flow-through reactor is lessened or discontinued. The flow of oxidant through the flow-through reactor is lessened or discontinued.

During a second time interval, hydrocarbon reactant is passed through the flow-through reactor system, the hydrocarbon reactant which comprises, e.g., $C_{5-}$ hydrocarbon such as methane. At least a portion of the stored oxygen is released from the oxygen storage material, and the released oxygen reacts with at least a portion of the hydrocarbon reactant's hydrocarbon in the presence of the hydrocarbon conversion catalyst to produce a reaction mixture. The first reaction mixture comprises $C_{2+}$ composition produced from the alkane by one or more of catalytic oxygen coupling and catalytic oxydehydrogenation of the alkane and/or any coupled alkane. At least a portion of the reaction mixture is conducted away from the flow-through reactor.

In particular aspects, the flow-through reactor comprises (i) a hydrocarbon conversion catalyst having at least one of oxidative coupling functionality and oxydehydrogenation functionality, (ii) an oxygen storage material, and (iii) thermal mass. During a first time interval, a flow of oxidant is introduced into the flow-through reactor, and at least a portion of the oxidant's oxygen is transferred to the oxygen storage material for storage. At least one of (i) the transferring of oxygen from the oxidant and (ii) the storing of the transferred oxygen can be accompanied by a transfer of heat to or away from the thermal mass depending on (the thermal mass's initial temperature and whether the oxygen transfer/storage is net endothermic or net exothermic.) The first flow is lessened or substantially halted. A second flow comprising methane is then transferred to the flow-through reactor. Additional heat is transferred to the thermal mass. At least a portion of the oxygen storage material's stored oxygen is released, and at least a portion of the released oxygen reacts with at least a portion of the second flow's methane in the presence of the first hydrocarbon conversion catalyst to produce ethylene. The reaction of the methane and the released oxygen is typically net exothermic, and at least a portion of any heat released from the exothermic reaction is transferred to the thermal mass. The process can be operated continuously, with a first time interval, followed by second time interval, followed by a repeated first time interval, followed by a repeated second time interval, etc. When the reaction of the second time intervals is net exothermic, the composition and amount of oxidant and the composition of the oxygen storage material can be selected to transfer to the oxygen transfer/storage reaction (during the first intervals) sufficient heat from the thermal mass to maintain the process in thermal balance. When the reaction of the second time intervals is net endothermic, the composition and amount of oxidant and the composition of the oxygen storage material can be selected to transfer away from the oxygen transfer/storage reaction (during the first intervals) sufficient heat to the thermal mass to maintain the process in thermal balance.

In other aspects, the invention relates to a flow-through reactor for producing a $C_{2+}$ composition. The flow-through reactor comprising (a) a first region having a first thermal mass segment and a first aperture, (b) a second region having a second thermal mass segment and a second aperture, and a catalytic conversion zone containing catalyst having oxidative coupling functionality and/or oxydehydrogenation functionality. At least one of the first and second thermal mass comprises oxygen storage material. The first and second regions are configured for flowing a feed mixture to enter the reactor proximate to the first aperture, with one or more components of a reaction mixture exiting the reactor proximate to the second aperture. The flow-through reactor can be a uni-flow or reverse-flow reactor. In another aspect, the invention relates to a system and method for producing $C_{2+}$ composition, particularly a $C_{2+}$ olefin composition, and more particularly ethylene and/or propylene.

Figures 1A, 1B:
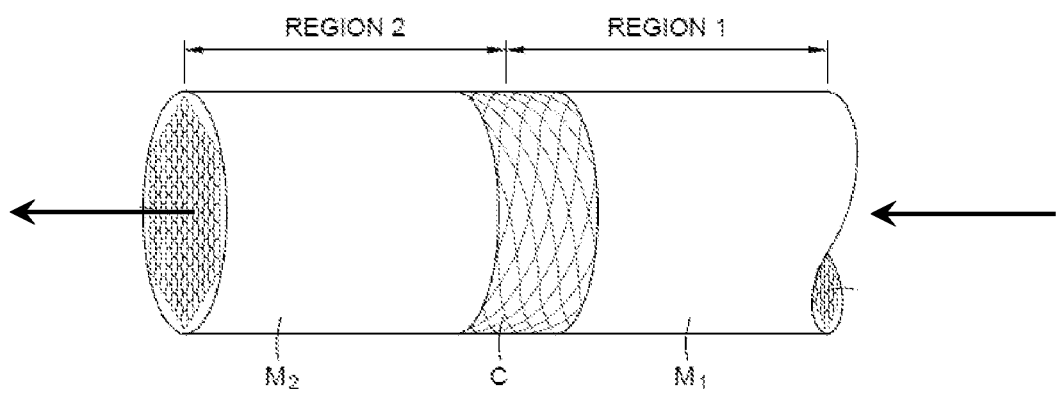
FIG. 1A is an example of a flow-through reactor, which includes a thermal mass, at least one oxygen storage material and at least one hydrocarbon conversion catalyst.
FIG. 1B is as simplified sectional enlargement of a reaction of a thermal mass which includes oxygen storage material, in which "M" refers to a metal center, representative of at least one oxygen storage material, and "O" refers to oxygen from an oxidant, which has been stored in the oxygen storage material.

Although the invention can be described in terms of a hydrocarbon conversion process, particularly and oxygen storage/release process and a catalytic hydrocarbon conversion process, for producing olefins such as ethylene and propylene, the invention is not limited thereto. In other words, to the extent that the following detailed description is specific to a particular embodiment or a particular use, this is intended to be illustrative only, and is not to be construed as limiting the scope of the invention. On the contrary, it is intended to cover all alternatives, modifications and equivalents that may be included within the spirit and scope of the invention.

DETAILED DESCRIPTION OF THE INVENTION

I. Introduction and Definitions

Certain aspects of the invention relate to one or more of a reactor, reaction process, and reaction system for contacting hydrocarbon reactant in the presence of oxygen stored and released within the reactor, and catalytically converting at least a portion of alkane, e.g., methane, in the hydrocarbon reactant with the released oxygen to produce a reaction mixture comprising a $C_{2+}$ composition. While not wishing to be bound by any theory or model, it is believed that the conversion is primarily the result of (i) one or more oxidative coupling reactions when the hydrocarbon reactant comprises methane and/or (ii) one or more oxydehydrogenation reactions when the hydrocarbon reactant comprises $C_{2+}$ alkane.

Oxygen storage and release for carrying out the catalytic conversion is achieved using an oxygen storage material. In certain aspects, a thermal mass is utilized which comprises, consists essentially of, or consists of oxygen storage material. Oxygen is transferred from a flow of oxidant to the oxygen storage material for storage with the oxygen storage material. Oxygen is typically transferred and stored as the oxidant flow passes through the reactor. Oxygen can be transferred from the oxidant to the oxygen storage material for storage with the oxygen storage material can be in any form, e.g., as oxygen atoms, oxygen ions, or as a component of an oxygen-containing molecule (e.g., an oxygen precursor). Stored oxygen released from the oxygen storage material for reacting with the hydrocarbon reactant to produce the first reaction mixture can be in any form, e.g., as oxygen atoms, oxygen ions, or as a component of an oxygen-containing molecule (e.g., an oxygen precursor).

Storage of the oxygen can cause the thermal mass to be heated. For example, storage of the oxygen can be accompanied by exothermic reaction with the thermal mass. Thus, the oxidant itself can be considered a heating fluid for heating the flow-through reactor.

Alternatively or in addition, a hydrocarbon fuel can be included with the oxidant, e.g., as components of a heating fluid. The hydrocarbon fuel can be combusted to produce a combustion gas, with additional heat being transferred to the thermal mass. The heating fluid can contain oxygen at a stoichiometric excess for substantially complete combustion with the hydrocarbon fuel, and at least a portion of the oxygen from the oxidant can be transferred to the oxygen storage material for storage and subsequent release. Alternatively, or in addition, heat can be transferred to the oxidant in the flow-through reactor or upstream thereof to produce a heating fluid.

In certain aspects, the invention relates to a reaction system that includes a reactor comprising: (i) a first region having a first thermal mass segments and a first aperture; (ii) a second region having a second thermal mass segment and a second aperture, and (iii) a catalytic conversion zone containing catalyst having an oxidative coupling functionality, oxydehydrogenation functionality or both, with the conversion zone further including an oxygen storage material. At least a portion of the catalyst and oxygen storage material can be deposited on or in at least one of the first thermal mass segment and second thermal mass segment. The first and second regions can be configured for transferring a first flow of an oxidant to enter the reactor proximate to the first aperture during a first time interval. The first and second regions can be configured for transferring a second flow of a hydrocarbon reactant to enter the reactor proximate to the first aperture during a second time interval. The first and second regions can be further configured to flow one or more components of a reaction mixture to exit the reactor proximate to the second aperture.

Optionally, the reactor can be a reverse-flow reactor. For example, the reverse-flow reactor can be further configured for flowing a second flow of an oxidant and a second flow of a hydrocarbon reactant to enter the reactor proximate to the second aperture, with one or more components of a second reaction mixture exiting the reactor proximate to the first aperture. Alternatively, or in addition, For example, the reverse-flow reactor can be configured for flowing a second flow of an oxidant to enter the reactor proximate to the second aperture during a first time interval, and a second flow of a hydrocarbon reactant to enter the reactor proximate to the first aperture during a second time interval. One or more components of a second reaction mixture then exit the reactor proximate to the first aperture.

Besides the $C_{2+}$ composition, the reaction mixture typically further comprises unconverted alkane and/or $CO_2$ produced during the alkane conversion. At least a portion of the reaction mixture's $C_2$ composition can be removed by exposing the reaction mixture to at least one $C_2$ selective sorbent. Using a $C_2$ selective sorbent allows the removal and recovery of $C_2$ components from the reaction mixture, especially ethylene, at temperatures $\geq 0°$ C., such as $\geq 50°$ C., or $\geq 100°$ C., or $\geq 150°$ C., or $\geq 200°$ C. In other words, using a $C_2$ selective sorbent substantially obviates the need for cryogenic separation of $C_2$ compounds from the reaction mixture.

Exposing the reaction mixture to at least one $C_2$ selective sorbent results in the selective sorption of at least a portion of any $C_2$ hydrocarbon in the reaction mixture's $C_{2+}$ composition. This produces a $C_2$ lean mixture, which comprises at least a portion of the unconverted alkane. The $C_2$ lean mixture is "lean" in the sense that it has a $C_2$ content that is less than that of the reaction mixture. Although optional, it is further efficient to remove at least a portion of the reaction mixture's $CO_2$ upstream of the separating at least a portion of the reaction mixture's $C_2$ composition upstream of the $C_2$ selective sorbent. Doing so beneficially lessens the vapor load on the $C_2$ selective sorbent, and also allows for the use of process equipment (e.g., conduits, sorbent containment vessels, compressors, etc.) with significantly smaller hydraulic capacity. For generally the same reasons, it is beneficial to remove any water present in the reaction mixture before the reaction mixture is exposed to the $C_2$ selective sorbent.

In certain embodiments, the invention relates to a reaction system that includes a reactor, such as a reverse-flow reactor, and a $C_2$ selective sorption system. For example, a $C_2$ selective sorption system can be configured in fluid communication with the first aperture, and optionally second aperture, for receiving at least a portion of the catalytically converted reaction mixture, and optionally the second reaction mixture. The $C_2$ selective sorption system can include a $C_2$ selective sorbent, which can be used to non-cryogenically recover the $C_2$ compositions in the reaction mixtures.

The invention is not limited to these aspects, and this description is not meant to foreclose the use of other reactors and/or other hydrocarbon reactants within the broader scope of the invention. For the purpose of this description and appended claims, the following terms are defined:

The term "hydrocarbon" means compounds containing hydrogen bound to carbon, and encompasses (i) saturated hydrocarbon, (ii) unsaturated hydrocarbon, and (iii) mixtures of hydrocarbons, including mixtures of hydrocarbons (saturated and/or unsaturated) having different values of n.

The term "$C_n$" hydrocarbon wherein n is a positive integer, e.g., 1, 2, 3, 4, or 5, means hydrocarbon having n carbon atom(s) per molecule.

The term "$C_{n+}$" hydrocarbon wherein n is a positive integer, e.g., 1, 2, 3, 4, or 5, means hydrocarbon having at least n carbon atom(s) per molecule.

The term "$C_{n-}$" hydrocarbon wherein n is a positive integer, e.g., 1, 2, 3, 4, or 5, means hydrocarbon having no more than n number of carbon atom(s) per molecule.

The term "alkane" means substantially saturated compounds containing hydrogen and carbon only, e.g., those containing $\leq 1\%$ (molar basis) of unsaturated carbon atoms. The term alkane encompasses $C_1$ to $C_5$ linear, iso, and cyclo alkanes.

The term "$C_n$ unsaturate" means a $C_n$ hydrocarbon containing at least one carbon atom directly bound to another carbon atom by a double or triple bond.

The term "Periodic Table" means the Periodic Chart of the Elements, as it appears on the inside cover of The Merck Index, Twelfth Edition, Merck & Co., Inc., 1996.

The term "oxidant" means any oxygen-bearing material which, under the conditions in the reaction zone, yields an oxygen for transfer to the oxygen storage material, for storage with and subsequent release from the oxygen storage material to the oxidative coupling and/or oxydehydrogenation. While not wishing to be limited to theory, molecular oxygen atoms may be provided as a reactive gas in a gaseous zone and/or atomic oxygen may be provided from a catalyst surface as, for instance, reacted, sorbed forms.

The term "oxidative coupling" refers to the oxygen-assisted dehydrogenation and coupling (formation of C—C bonds) of alkane (particularly methane) to produce water and hydrocarbon of higher order, such as producing $C_2$ hydrocarbon from methane. The term "oxydehydrogenation" means oxygen-assisted dehydrogenation of an alkane, particularly a $C_{2+}$ alkane, to produce an equivalent alkene and water without coupling.

The term "oxidative coupling reactor," as used herein, refers to a reactor, or combination or system thereof for catalytically converting a feed containing alkane and oxidant to a composition containing $C_{2+}$ olefin. An oxidative coupling reactor optionally includes one or more reactors and/or associated equipment and lines, e.g., one or more reverse-flow reactors and interconnecting lines.

The term "residence time" means the average time duration for non-reacting (non-converting by oxidative coupling) molecules (such as He, N$_2$, Ar) having a molecular weight in the range of 4 to 40 to traverse the reactor or a defined zone within the reactor, such as a reaction zone of a oxidative coupling reactor.

The term "reaction stage" or "reactor stage" means at least one flow-through reactor, optionally including means for conducting one or more feeds thereto and/or one or more products away therefrom.

With respect to flow-through reactors, the term "region" means a location within the reactor, e.g., a specific volume within the reactor and/or a specific volume between a flow-through reactor and a second reactor, such as a second flow-through reactor. With respect to flow-through reactors, the term "zone", refers to a specific function being carried out at a location within the flow-through reactor. For example, a "reaction zone" or "reactor zone" is a volume within the reactor for conducting at least one of oxidative coupling and oxydehydrogenation. Similarly, a "quench zone" or "quenching zone" is a location within the reactor for transferring heat from products of the catalytic hydrocarbon conversion, such as C$_{2+}$ olefin.

The term "flow-through reactor" refers to a reactor design in which feed can flow through the reactor, with the oxidant and hydrocarbon reactant feeds coming into contact with the conversion catalyst and oxygen storage material as the feed flows through the reactor.

The term "tubular reactor" means an elongated reactor vessel of substantially any cross-section, the vessel being configured to allow fluid flow into, though, and out of the vessel, via first and second apertures, the first and second apertures being located proximate to opposed ends of the elongated reactor vessel.

The term "fixed-bed catalytic reactor" means a catalytic reactor having at least one bed of catalyst, wherein the catalyst is substantially retained within the bed.

The term "catalytic oxidative coupling reactor" means a reactor in which oxidative coupling and/or oxydehydrogenation reactions are carried out. In such reactions, ≥30.0% of the heat utilized by the reactions are provided by heat transfer from reactor components, e.g., solid surfaces associated with the reactor, such as tubulars or bed materials. In a thermal catalytic oxidative coupling reactor, ≥50.0% of the heat utilized by the reactions are provided by heat transfer from reactor components, optionally ≥80.0% or ≥90.0%. Optionally, an exothermic reaction (e.g., combustion) occurs within the catalytic oxidative coupling reactor, e.g., for preheating and/or reheating one or more components of the flow-through reactor, e.g., first and/or second thermal mass segments.

The term "hydrocarbon conversion catalyst" means any catalyst having at least one of oxidative coupling functionality and oxydehydrogenation functionality.

A "C$_2$ selective sorbent" is a sorbent having a selectivity for [ethane+ethylene] sorption over that of methane that is greater than 1.0. When exposed under sorption conditions to a mixture comprising methane, ethane, and ethylene, C$_2$ selective sorbent having a selectivity for [ethane+ethylene] over methane of greater than 1.0 will retain >50% of the mixture's [ethane+ethylene] and ≤50% of the mixture's methane. When a C$_2$ selective sorbent has a selectivity for [ethane+ethylene] over that of methane of greater than 5.0, the sorbent will retain >83% of the mixture's [ethane+ethylene]. The C$_2$ selective sorbent can have, e.g., a selectivity for [ethane+ethylene] over methane ≥9, such as ≥99, or ≥999, or ≥9999.

II. Reactor Apparatus and Process

The reaction for converting alkane to a reaction mixture comprising C$_{2+}$ hydrocarbon is carried out in at least one reactor. In the present disclosure, a reactor refers to equipment used for chemical conversion. As such, several items identified as reactors may be combined to become a single entity that is also identified as a reactor, in that individual and combined entities may be characterized as equipment used for chemical conversion.

Main conversion reactions in the reaction zone section of the reactor, when the feed to the reactor comprises methane and oxygen, are the exothermic reactions to C$_2$ products:

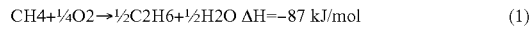

$$CH_4 + \tfrac{1}{4}O_2 \rightarrow \tfrac{1}{2}C_2H_6 + \tfrac{1}{2}H_2O \quad \Delta H = -87 \text{ kJ/mol} \tag{1}$$

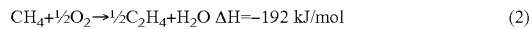

$$CH_4 + \tfrac{1}{2}O_2 \rightarrow \tfrac{1}{2}C_2H_4 + H_2O \quad \Delta H = -192 \text{ kJ/mol} \tag{2}$$

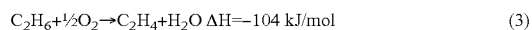

$$C_2H_6 + \tfrac{1}{2}O_2 \rightarrow C_2H_4 + H_2O \quad \Delta H = -104 \text{ kJ/mol} \tag{3}$$

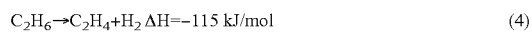

$$C_2H_6 \rightarrow C_2H_4 + H_2 \quad \Delta H = -115 \text{ kJ/mol} \tag{4}$$

and optionally combustion, which consumes more oxygen and generates more heat:

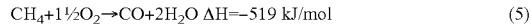

$$CH_4 + 1\tfrac{1}{2}O_2 \rightarrow CO + 2H_2O \quad \Delta H = -519 \text{ kJ/mol} \tag{5}$$

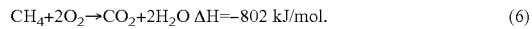

$$CH_4 + 2O_2 \rightarrow CO_2 + 2H_2O \quad \Delta H = -802 \text{ kJ/mol}. \tag{6}$$

It has been found that by regulating oxygen storage and the relative flow of reactant and oxidant, reactions (1)-(4) can be favored over reactions (5) and (6), and over reactions which combust one or more of the desired products. Such undesirable combustion reactions include C$_2$H$_x$+O$_2$→CO$_2$+H$_2$O, such as C$_2$H$_4$+3O$_2$→2CO$_2$+2H$_2$O (−1412 KJ/mol) and C$_2$H$_6$+$\tfrac{7}{2}$O$_2$→2CO$_2$+3H$_2$O (−1517 KJ/mol). An advantage of the invention is that coke deposited during catalytic hydrocarbon conversion reactions can be removed from inside the reactor during a subsequent oxygen-storage step.

The desired reactions i.e., (i) oxidative coupling reactions and/or oxydehydrogenation reactions are carried out in the presence of the specified hydrocarbon conversion catalyst, and are believed to be catalytic processes. The hydrocarbon conversion is carried out in the presence of stored oxygen released from the oxygen storage material. The hydrocarbon conversion catalysts and oxygen storage material can be located in one or more thermal masses of the reactor, with the conversion reactions being carried out at temperatures and pressures effective for converting alkane to the specified reaction mixture. For example, the hydrocarbon conversion processes are observed to be particularly efficient when carried out at reaction zone temperatures of from 550° C. to 1100° C. Alternatively, the overall hydrocarbon conversion process to produce the C$_{5+}$ hydrocarbon is particularly efficient at reaction zone temperatures of from 650° C. to 900° C., or at temperatures of from 675° C. to 825° C.

Operating pressures may include a pressure of at least atmospheric pressure (zero pressure, gauge), such as ≥4 pounds per square inch gauge (psig) (28 kilo Pascals gauge (kPag)), or ≥15 psig (103 kPag), or ≥36 psig (248 kPag), or ≥44 psig (303 kPag), or ≥103 psig (709 kPag), but may be ≤300 psig (2064 kPag), or ≤163 psig (1121 kPag), or ≤150 psig (1032 kPag).

Residence times in the flow-through reactor may be ≤20 seconds, ≤10 seconds and preferably ≤5 seconds or in the range of 0.01 seconds to 20 seconds or in the range of from 0.5 seconds to 10 seconds. For a reverse-flow reactor, the process may operate at cycle times ≥0.5 second, such as in the range of 10 seconds to 240 seconds, in the range of 10 seconds to 120 seconds, in the range of 20 seconds to 60 seconds, or in the range of 20 seconds to 40 seconds. The term "cycle time" means the time from a first interval to the next first interval, including (i) intervening second, third, and/or fourth intervals and (ii) any dead-time between any pair of intervals.

Also, as may be appreciated, these different pressures and temperatures may be utilized together to form different combinations depending on the specific configuration of equipment.

Any flow-through reactor can be used which is suitable can be used for carrying out oxidative coupling reactions and/or oxydehydrogenation reactions. For example, fixed-bed catalytic reactors can be used. Examples of fixed-bed catalytic reactors include fixed-bed tubular reactors.

As a first step, or during a first time interval, oxidant is passed through the flow-through reactor. The flow-through reactor is maintained under conditions of temperature, pressure, and flow sufficient to transfer oxygen from the oxidant to the oxygen storage material and to store the transferred oxygen with the oxygen storage material. When additional heat is needed, this can be provided to the flow-through reactor by one or more of (i) heating the oxidant upstream of or in the flow through reactor, (ii) selecting the oxidant and/or oxygen storage material, and (iii) introducing a hydrocarbon fuel into the flow-through reactor with the oxidant to combust and exothermically release heat. When the oxidant provides heat to the flow-through reactor, the oxidant can be referred to as "heating fluid". Heating fluid can be utilized, e.g., when the oxygen transfer and/or storage are net exothermic, but not sufficiently exothermic to provide sufficient heat transfer to and from the reactor's thermal mass for a subsequent endothermic catalytic hydrocarbon conversion.

When the oxygen transfer/oxygen storage is net exothermic, oxygen is transferred from the oxidant to the oxygen storage mate to heat the thermal mass. Oxygen from the oxidant is stored with the oxygen storage material as the oxidant is passed through the reactor, with at least a portion of the heat produced during the oxygen transfer storage being transferred to the flow-through reactor, e.g., to the flow-through reactor's thermal mass. Oxidant flow is lessened or stopped after (i) sufficient oxygen is stored with the oxygen storage material for carrying out the specified first catalytic hydrocarbon conversion and (ii) sufficient heat is added (if any is needed) for carrying out the specified oxygen transfer/storage and the specified first and second catalytic hydrocarbon conversions.

During a subsequent or second time interval, hydrocarbon reactant is passed through the flow-through reactor under conditions of pressure, temperature and flow sufficient for releasing at least a portion of the oxygen that was transferred to and stored with the oxygen storage material during the first time interval. As the hydrocarbon reactant flows through the reactor, at least a portion of the hydrocarbon reactant reacts with at least a portion of the released oxygen in the presence of at least the hydrocarbon conversion catalyst to produce the reaction mixture. When additional heat is needed for the reacting, one or more of (i) the type and/or amount of hydrocarbon reactant and (ii) the reacting conditions are selected so that the additional heat is released during at least part of the second time interval. For example, the flow-through reactor can configured to release weakly-bound stored oxygen proximate to the surface of the oxygen storage material, which weakly-bound oxygen then exothermically reacts with the hydrocarbon reactant. At least a portion of the heat released during this exothermic reaction can be transferred to the oxygen storage material to assist in the release of more tightly-bound stored oxygen within the oxygen storage material.

The reacting of the hydrocarbon reactant with the released oxidant in the presence of the first hydrocarbon conversion catalyst produces a reaction mixture comprising (i) a $C_{2+}$ composition, (ii) water, and (iii) any molecular hydrogen, (iv) at least a portion of any diluent, and (v) at least a portion of any unreacted hydrocarbon reactant. It is surprisingly found that the amount of stored oxygen released and reacted with the hydrocarbon reactant under the specified conditions is in a desired range for favoring reactions (1)-(4) over reactions (5) and (6), and over reactions which combust hydrocarbon in the reaction mixture.

When the hydrocarbon reactant comprises $C_{5-}$ alkane, the $C_{2+}$ composition typically comprises ≥1.0% olefin (weight basis), e.g., ≥5.0% olefin, such as ≥10.0% olefin. The type and amount of components of the $C_{2+}$ composition typically depend on the hydrocarbon reactant's composition. When the hydrocarbon reactant comprises ≥90% methane (weight basis), the $C_{2+}$ composition typically comprises ≥25% (weight basis) of $C_2$ hydrocarbon, e.g., ≥50% [ethane+ethylene], such as ≥75% [ethane+ethylene], or ≥90% [ethane+ethylene].

Oxidant and hydrocarbon reactant can be flowed in the same direction in the flow-through reactor ("uni-flow"), provided each flow is carried out during separate time intervals. For example, during a first time interval a heating fluid (e.g., pre-heated oxidant and/or oxidant heated in the flow-through reactor during the first time interval by combustion of a portion of the oxidant with a hydrocarbon fuel) can be flowed in a forward direction. During a second or subsequent time interval, the hydrocarbon reactant can be flowed in the forward direction through the flow-through reactor.

If desired, when the heating fluid includes an oxidant and hydrocarbon fuel, and a combustion gas is produced by oxidant combustion with a hydrocarbon fuel, a sweep fluid can be passed through the flow-through reactor to remove at least a portion any combustion gas that might remain within the reactor. The sweep fluid can be passed through the reactor during a time interval between the first time interval and the second time interval. The sweep fluid can be passed in the forward direction or the reverse direction. Typical sweep fluids include relatively inert liquids and vapors, especially those which are relatively easy to separate from the desorbed $C_{2+}$ composition. Steam and/or molecular nitrogen are examples of suitable sweep fluids.

The thermal mass of the flow-through reactor can comprise a first thermal mass segment and a second thermal mass segment. In such embodiments, during the second time interval, the first thermal mass segment can be heated and the second thermal mass segment can be cooled as the catalytic conversion is continued. Oxygen stored with the oxygen storage material can be endothermically released from the thermal mass during the second time interval, contributing to the cooling.

Reverse-flow catalytic reactors can be used to carry out the first and second catalytic hydrocarbon conversions, including one or more conventional reverse-flow reactors. Reactors typically used for converting or cracking reactions, and to execute cyclic, high temperature chemistry, can be used, such as those described in U.S. Pat. Nos. 7,943,808, 7,491,250, 7,846,401, and 7,815,873.

Generally, forward and reverse flows through reverse-flow catalytic reactors are carried out during separate time intervals. For example, the heating fluid can be flowed in a first or forward direction through the reverse-flow reactor, during a first time interval. During a second or subsequent time interval, the hydrocarbon reactant can be flowed in a second or reverse direction through the reverse-flow reactor.

Regenerative, reverse-flow catalytic oxidative coupling reactors can be used to carry out oxidative coupling and/or oxydehydrogenation reactions. A regenerative, reverse-flow reactor is (i) "reverse flow" in the sense that an upstream region of the reactor with respect to the average flow of the first feed mixture corresponds to the downstream region with respect to the average flow of the second feed mixture and (ii) "regenerative" in the sense that at least a portion of any heat lost (e.g., by radiation) during a time interval is restored by heat released during a subsequent interval (and vice versa). For example, combusting at least a portion of the heating fluid's hydrocarbon fuel with a portion of the heating fluid's oxidant can provide heat to the reverse-flow reactor's thermal mass during the first time interval. Heat can be withdrawn from the thermal mass to when the catalytic hydrocarbon conversion reactions is net endothermic, which can substantially restore the reverse-flow reactor's temperature profile to that subsisting at the start of the first time interval. The first and second time intervals can then be repeated, one after the other. Hydrocarbon deposits formed during the specified hydrocarbon conversion (e.g., coke deposits in the reverse-flow reactor) during the second time interval, can be removed by combustion with a portion of the heating fluid's oxidant during a subsequent first time interval. This can lessen the amount of hydrocarbon fuel needed in the heating fluid, and can substantially prevent the accumulation of hydrocarbon deposits in the reverse-flow reactor. Heat can be transferred to and stored with the reverse-flow reactor during the first and second time intervals, e.g., by transferring heat within a defined volume (e.g., the first and/or second thermal mass segments).

A variety of flow-through reactors are suitable. The flow-through reactor can be physically symmetric, e.g., a reverse-flow reactor that is symmetric about a central axis. The flow-through reactor can be adiabatic, e.g., an adiabatic reverse-flow reactor. The flow-through reactor can include a housing, a plurality of flow-control means (e.g., conduits and valves), one or more insulation components (e.g., insulation bricks) and one or more process flow components (e.g., thermal mass, mixing components, etc.). The housing may be utilized to enclose an interior region and has one or more insulation components disposed adjacent to the housing. The plurality of flow control means may include one or more conduits, one or more apertures, and one or more valves that are configured to manage the flow of one or more streams into and out of the interior region from a location external to the interior region or housing. Process flow components can be configured and/or arranged to manage the flow of fluids through the interior region, wherein the one or more process flow components may include a thermal mass having different portions with each having different flow passages and a wetted area. In embodiments where the first and/or second mixtures are combined in a reverse-flow reactor, one or more mixer or mixer-distributors can be used for the mixing.

Regenerative reverse-flow reactors may involve multiple steps repeated in sequence to form a cycle for the process. For example, the process can include two or more sequential steps, such as two or more steps operated continuously in sequence (one step after the other). The steps can include, e.g., (i) a net endothermic, forward-flow hydrocarbon conversion step, (ii) a net exothermic, reverse-flow, oxygen transfer/storage and reactor regeneration step, (iii) a repetition of the forward-flow hydrocarbon conversion step, and (iv) a repetition of the reverse-flow oxygen transfer/storage and reactor regeneration step. The steps may involve passing mixtures over a solid material in fixed orientation (e.g., one or more thermal masses). As part of these steps, valves may be utilized to alternate introduction of feed mixtures into the reactor, e.g., a first feed mixture comprising hydrocarbon reactant and a second feed mixture comprising oxidant-containing heating fluid.

As an example, regenerative reactors can deliver a heating fluid comprising hydrocarbon fuel and oxidant, with the oxidant's oxygen content being at a stoichiometric excess for substantially complete combustion with the hydrocarbon fuel, directly to a location along the flow path within the reactor (e.g., a mixing zone). At least a portion of the heating fluid's hydrocarbon fuel combusts, transferring heat to the flow-through reactor, e.g., to the reactor's thermal mass. The combustion reaction can be carried out to heat the thermal masses before, during and/or after one or more intervals of the oxidative coupling reaction. For example, a combustion reaction can be carried out to initially heat (e.g., preheat) one or more thermal masses of the reverse-flow reactor. Combustion products can then be exhausted using a sweep fluid. A flow of sweep fluid can be established during the same time interval as which the heating fluid flow is established through the flow-through reactor, or alternatively or in addition, during a subsequent time interval occurring before (or during) which a flow of hydrocarbon reactant through the flow-through reactor is established. Following reactor regeneration and oxygen transfer/storage, the hydrocarbon reactant flow is established through the reactor. Hydrocarbon reactant is exposed to the reactor's heated thermal mass, and heat can be transferred between the thermal mass and the hydrocarbon reactant for (i) releasing oxygen stored with the oxygen storage material and (ii) the catalytic reaction of the hydrocarbon reactant with the released oxygen, to produce the reaction mixture. The reaction mixture can be quenched in the flow-through reactor. Quenching can be accomplished, e.g., by transferring heat to a cooler region of the reactor, obviating the need for an external quench as in conventional processes. For example, the reactor can contain a cooler thermal mass (a second thermal mass or segment of the thermal mass that is cooler than the reaction mixture) located downstream of the catalytic hydrocarbon conversion reaction. In operation, the second thermal mass segment absorbs heat from the reaction mixture during a time interval (during hydrocarbon reactant flow), sufficient to (i) cool the reaction mixture and (ii) impart heat to the heating fluid (when the flow is reversed) during a subsequent time interval.

The reactor may include reactor components, such as process flow components (e.g., reactor components used to manage the flow of mixtures through the reactor, one or more of the thermal masses for absorbing, storing and releasing heat, catalyst, sorbent, and/or mixing component) and insulation components (e.g., reactor components used to manage the heat transfer from the process flow within the reactor to the external surface of the reactor, such as insulation bricks, tiles or packing). The reactor components may be formed from different materials, such as refractory support materials, which can be used to support the catalyst and sorbent.

Heat generated during one or more the conversion step, e.g., one or more of (i) oxygen transfer/storage, the first catalytic hydrocarbon conversion, and (iii) the second catalytic hydrocarbon conversion can be stored in a thermal mass material. The thermal mass material is one that is designed or adapted to facilitate storage and utilization of heat. The oxygen storage material and/or the hydrocarbon conversion catalyst can be utilized as thermal mass. Additional thermal mass can be associated with the flow-through reactor if needed, e.g., in cases where the insufficient thermal mass is provided by the oxygen storage material and the hydrocarbon conversion catalyst.

The thermal mass typically comprises material (e.g., a solid material) that can transfer (e.g., absorb, store, and release) thermal energy over a temperature range for carrying out the reverse flow cycle, which includes the oxidative coupling reaction and any optional combustion reaction. For example, the thermal mass can be a solid material that can absorb, release, and store heat from reactants and products over a temperature range in which oxidative coupling can be carried out, including those that do so without any significant phase change. In particular embodiments, the solid material can absorb and store heat and release the stored heat, without any significant phase change, over a temperature range in which oxidative coupling and hydrocarbon combustion are carried out. Examples of temperature ranges at which the thermal mass absorbs, stores and releases thermal energy include a range of from 50° C. to 1500° C., alternatively from 100° C. to 1500° C. or from 200° C. to 1500° C. The thermal mass can be characterized by one or more properties. Examples of such properties include melting temperature, porosity, bulk density, thermal conductivity, thermal expansion and thermal capacity.

Checker bricks, tiles, and monoliths may be used as to form the thermal mass components within the reactor. Such materials form a network of passages that are used by the gases in each step to transit the region containing solid material. The thermal mass may be a ceramic, which may include yttria, zirconia, alumina, and/or other refractory material capable of adsorbing, storing and transferring heat, and that are effective in withstanding temperatures within the oxidative coupling reactor.

In certain embodiments, one or more of the thermal masses includes separate passages through reactor components to manage the flow of hydrocarbon components and or oxidant through the thermal mass. Preferably, each thermal mass includes separate passages. The separate flow passages in the thermal mass can further comprise flow barriers that effectively function as walls to lessen or prevent cross flow or mixing of fluids (e.g., reactants, oxidants, and/or products) between passages, except in the desired regions of the reactor. Each thermal mass preferably includes a plurality of passages (called "channels"), which may preferably be in parallel flow arrangement. The channeled thermal mass may preferably be comprised of one or more honeycomb monoliths. Preferred honeycomb monoliths are structures that comprise many (e.g., a plurality, meaning more than one) fluid-flow passages, arranged in parallel fashion with walls serving to separate each passage. Such reactor can include a single monolith or a plurality of monoliths. Each monolith can be formed by extruding or die pressing monolith blocks with shaped (e.g., square or hexagonal) cross-section and two- or three-dimensionally stacking, such blocks above, behind, and beside each other. Monoliths are particularly effective as thermal mass because they provide high heat transfer capacity with lessened pressure drop.

III. Oxygen Storage Material

The reactor includes at least one oxygen-storage material, namely a material having functionality for transferring at least a portion of the oxidant's oxygen, storing the transferred oxygen, and releasing at least a portion of the stored oxygen under the specified conditions. The oxygen storage material can be a material having oxygen-sorptive capacity, as well as the ability to release the sorbed oxygen, particularly at elevated temperatures. The oxygen storage material can comprise a metal oxide, for example a transition metal oxide, having a reversible sorptive affinity for oxygen at elevated temperature. Such materials include those that sorptively remove and release oxygen from oxidant and those that undergo a chemical and/or physical change in the course of reversible oxygen storage.

As used herein, the term "elevated temperature" means a temperature in the range of from 400° C. to 1000° C. As used herein, the term "high sorptive capacity" means an oxygen storage capacity of at least 40 millimoles of oxygen per mole of the oxygen storage material that contacts the oxidant at a temperature of 800° C.

The oxygen storage material can be utilized as materials mixed with or coated onto a support or substrate. For example, the oxygen storage material can be utilized as finely divided materials as a part of a thermal mass or as one or more coatings on a thermal mass substrate to provide a material having oxygen-storage functionality.

A thermal mass comprising material having oxygen-storage functionality can be used to temporarily store an oxygen at relatively high temperatures for use in the overall catalytic hydrocarbon conversion reactions to produce the specified $C_{2+}$ reaction mixture. For certain oxygen storage materials, as the temperature of the thermal mass is lessened, oxygen is more easily transferred to the oxygen storage material. In other oxygen storage materials, as the temperature of the thermal mass is lessened, oxygen is more easily released from the oxygen storage material. Heat transfers needed for (i) transferring and/or storing oxygen and (ii) for the specified hydrocarbon conversion reactions can include the transfer of heat to/from the reactor's thermal mass.

In certain aspects, a thermal mass comprising oxygen storage material is heated to a relatively high temperature. As oxidant contacts the heated thermal mass over a first time interval, oxygen is transferred to and stored with the oxygen storage material. During a second time interval, hydrocarbon can be contacted with stored oxygen released from the heated oxygen storage material, with the hydrocarbon being further heated by the heated thermal mass. As the heated hydrocarbon and released oxygen contact the hydrocarbon conversion catalyst, at least a portion of the hydrocarbon (e.g., methane) is catalytically converted to produce a first reaction mixture. Although the hydrocarbon conversion reaction can be exothermic, release of the oxygen under continued contact and reaction with the hydrocarbon can be carried out under overall (net) endothermic conditions. This means that oxygen can be more readily released over time, as the release of the oxygen and reaction with the hydrocarbon will ultimately decrease thermal mass temperature. This decrease in temperature gradually eases oxygen release from the oxygen storage material, which lessens the amount of combustion of hydrocarbon reactant with released oxygen that would otherwise occur.

In certain aspects, the oxygen storage material can enable the bulk separation and purification of oxygen based on ionic transport, in which the oxygen storage material is maintained at high temperature to temporarily store oxygen. Oxygen that contacts the surface of the oxygen storage material can be decomposed on the surface of the material and incorporated into the crystalline lattice of the material. Storage of the oxygen can be particularly facilitated over the temperature range from 400° C. to 1000° C. A featured of the process is that oxygen transfer, storage, and release can be carried out continuously under the specified process conditions without appreciable decomposition of the oxygen storage material.

In certain aspects, when oxidant contacts the oxygen storage material, oxygen in the oxidant can be adsorbed and dissociated, with charge transfer acting to cause penetrative flux of the oxygen species into the oxygen storage material. A chemical potential driving force can be employed to effect ionic transport of the oxygen species into the oxygen storage material.

Depending on the oxidant and oxygen storage material used, the transfer of oxygen to the oxygen storage material and the storage of the oxygen with the oxygen storage material can be net exothermic or net endothermic. Thus, oxygen transfer to the oxygen storage material and storage of oxygen with the oxygen storage material can include a transfer of heat to or from one or more of (i) the oxidant storage material, (ii) the hydrocarbon conversion catalyst, or (iii) a thermal mass. When the oxygen storage material is a component of a thermal mass, the oxygen storage material can be coated onto, mixed with, or otherwise associated with the thermal mass.

The oxygen storage material can be of any suitable size, shape and conformation appropriate to oxygen storage and conversion of hydrocarbon. For example, the material can be in a finely divided form, e.g., beads, spheres, rings, toroidal shapes, irregular shapes, rods, cylinders, flakes, films, cubes, polygonal geometric shapes, sheets, fibers, coils, helices, meshes, sintered porous masses, granules, pellets, tablets, powders, particulates, extrudates, cloth or web form materials, honeycomb matrix monolith, composites (of the oxygen storage material with hydrocarbon conversion catalyst and/or thermal mass), including in comminuted or crushed forms.

In certain embodiments, the oxygen storage material can be formed by metal-organic chemical vapor deposition (MOCVD) on suitable supports or substrates, e.g., thermal masses, using appropriate precursors for the respective metal components of the oxygen storage material. Use of MOCVD allows relatively close control of stoichiometry and uniformity of coverage to be achieved. MOCVD can be used to deposit films of multicomponent oxygen storage materials with compositional reproducibility on the order of 0.1% and thickness uniformity of better than 5%.

Alternatively, the oxygen storage material can be formed as bulk articles, e.g., particles, by various manufacturing techniques. Such techniques include powder metallurgy, slurry metallurgy (slip casting, tape casting, etc.) and coextrusion.

Another alternative technique for forming the oxygen storage material can be a sol gel technique. Such technique can be advantageous when the oxygen storage material is deposited on an inert substrate, such as a thermal mass comprising porous silica, alumina, kieselguhr, or the like. Sol gel techniques can be employed to make up a sol of the precursor constituents of the oxygen storage material and to spray, dip-coat, soak, roller coat, or otherwise apply the solution to the substrate, e.g., the thermal mass. The coated substrate containing the precursor material can be subjected to high temperature, e.g., calcined, to produce the desired oxygen storage material.

Transition metal oxides are particularly useful as oxygen storage materials. Transition metals can be considered an IUPAC Group 3-12 element and elements of the Lanthanide series. Preferred oxygen storage materials can be oxides containing at least one Group 3, Group 6, Group 7, Group 8, Group 9 and Lanthanide series element. Examples of each these metals are shown in the Periodic Table.

Perovskites and related materials, such as perovskite-like materials and pyrochlores, can be particularly useful as oxygen storage materials. "Perovskites" can generally be considered oxygen-containing compounds having the crystal structure, $ABO_3$, with high-temperature $O^{2-}$ vacancies. Such structures can also be denoted by use of the symbol δ, according to the general formula $ABO_{3-\delta}$. The "A"-site cations can be rare earth (e.g., Lanthanide series including La and Y), alkaline earth (i.e., Group 2), alkaline (Group 1) and large cations such as $Pb^{2+}$, $Bi^{3+}$, or $Ce^{4+}$. The "B"-site cations can be 3d, 4d, or 5d transition-metal cations. Multiple cation-type occupations are possible. Framework sites "A" and "B" can be dodecahedral and octahedral, respectively, cf., L. G. Tejuca and J. L. Fierro, *Properties and Applications of Perovskite-type Oxides*, Marcel Dekker, New York, 1993.

A standard cubic high-temperature perovskite phase can remain stable and reversible with regard to changes of δ within a certain range: The value δ can be up to 0.25; for example δ can be from 0.05 to 0.25 (although higher values have been reported), at elevated temperature and low oxygen partial pressure, i.e., δ is a function of temperature and partial pressure of oxygen. Perovskite stability can be governed by cation radii of lattice metals in various valence states combined into a parameter "t" called "tolerance factor", cf., Z. Shao, et al., *Sep. Purif. Technol.*, 25 (2001) 419-42. A perovskite structure can be formed at t ranges from 0.75-1.

Examples of useful perovskites and perovskite structures can be found in U.S. Pat. No. 7,338,549. Such examples include, but are not limited to, those having the general formulas (1), (2), and (3):

$$A_xB_yO_{3-\delta}, \quad (1)$$

$$A_xA'_{x'}B_yB'_{y'}O_{3-\delta}, \quad (2)$$

$$A_xA'_{x'}A''_{x''}B_yB'_{y'}B''_{y''}O_{3-\delta}, \quad (3)$$

and combinations thereof, wherein:

A, A', and A" are independently selected from ions of atoms having atomic number ranging from 57-71, inclusive, a cation of yttrium, ions of Group 1 atoms, ions of Group 2 atoms, and combinations of two or more, where Group 1 and Group 2 refer to the periodic table of elements;

B, B', and B" are independently selected from d-block transition-metal ions selected from Mn, Cr, Fe, Co, Ni, and Cu;

x, x', x", y, y', and y" are each real numbers ranging from 0 to 1.0; and x+x'+x"=0.8-1.0; y+y'+y"=1.0; and δ ranges from about 0.05 to about 0.30.

Perovskite-like compounds useful in the invention are those having general formulas (4), (5), (6), (7), (8), and (9):

$$A_2BO_{4-\delta} \quad (4)$$

$$A_2B_2O_{5-\delta} \quad (5)$$

$$AO(ABO_{3-\delta})_n \quad (6)$$

$$AM_2Cu_3O_{7-\delta} \quad (7)$$

$$Bi_4V_{2(1-x)}Me_{2x}O_{11-3x}, \quad (8)$$

$$A''B''O_3 \quad (9)$$

wherein:

A is independently selected from ions of atoms having atomic numbers ranging from 57-71, inclusive, a cation of yttrium, ions of Group 1 atoms, ions of Group 2 atoms, and combinations of two or more, where Group 1 and Group 2 refer to the periodic table of elements;

B is independently selected from d-block transition metal ions;

A" is an ion of Na or Li, and B" is an ion of W or Mo;

M is a metal cation selected from cations of Group 2 atoms of the periodic table of elements;

Me is a metal cation selected from cations of Cu, Bi, and Co atoms;

x is a real number ranging from 0.01 to 1.0;
n ranges from 1 to about 10; and
δ ranges from about 0.05 to about 0.30.

Pyrochlores useful in the invention are those having general formula (10):

$$A_2B_2O_{7-\delta} \tag{10}$$

wherein:
A is independently selected from ions of atoms having atomic numbers ranging from 57-71, inclusive, a cation of yttrium, ions of Group 1 atoms, ions of Group 2 atoms, and combinations of two or more, where Group 1 and Group 2 refer to the periodic table of elements;
B is independently selected from d-block transition metal ions; and
δ ranges from about 0.05 to about 0.30.

Cerium-containing and praseodymium-containing metal oxides can also be used as the oxygen storage material. Examples of such materials include $CeO_2$, $Pr_6O_{11}$, $CeO_2$—$ZrO_2$, $CuO$—$CeO_2$, $FeO_X$—$CeO_2(1.0 \leq X \leq 1.5)$, $MnO_X$—$CeO_2(1.0 \leq X \leq 3.5)$, and $Pr_6O_{11}$—$CeO_2$.

In certain aspects, at least a portion of one or more of the thermal masses can include material having oxygen-storage functionality and a catalytic functionality. Such thermal masses are referred to herein as thermal masses comprising a catalyst composite.

Various arrangements of materials having oxygen-storage functionality and materials having catalytic functionality are within the scope of the invention. For example, the catalyst composite can be a mixed metal oxide comprising: 1) a first metal oxide having catalytic functionality for (i) oxidative coupling functionality and/or oxydehydrogenation functionality and 2) a second metal oxide having oxygen storage functionality. First and second metal oxides can be located proximate to thermal mass (e.g., in or on passages of a honeycomb monolith open to the flow of oxidant and hydrocarbon reactant), or may themselves function as thermal mass.

A first metal oxide having catalytic functionality for the specified catalytic hydrocarbon conversion reaction (oxidative coupling functionality and/or oxydehydrogenation functionality) can be in the form of catalyst particles, such as in a physical mixture of catalyst particles. Additional thermal mass, if needed can be included in the mixture, or (alternatively or in addition) the catalyst particles can be deposited on or in a thermal mass material in a location that is in diffusive contact with oxidant and hydrocarbon reactant. The second metal oxide having oxygen storage functionality can also be included with the physical mixture of catalyst and/or thermal mass, e.g., in a mixture with the thermal mass without catalyst; alternatively deposited on the thermal mass.

For example, in certain aspects, the flow-through reactor includes at least one composite, the composite comprising oxygen storage material and the hydrocarbon conversion catalyst. The composite can be in the form of particles, e.g., uniformly dispersed composite particles on or in a thermal mass. Alternatively, particles of oxygen storage material can be dispersed (e.g., substantially uniformly) among particles of the hydrocarbon conversion catalyst on or in a thermal mass. The composite can be in the form of a honeycomb monolith having at least one channel for establishing the specified flows of oxidant and hydrocarbon reactant.

The composite can be a physical mixture of oxygen storage material and hydrocarbon conversion catalyst. The composite can comprise additional thermal mass if needed. Oxygen storage material can be located in a particular location in the composite with respect to the location of the hydrocarbon conversion catalyst in the composite (e.g., a 'staged' composite). For example, the composite's components can be situated in a particular order with respect to the established flows. For example, the oxygen storage material can be located in a layer having a first side proximate to the established flows and a second side proximate to a layer of hydrocarbon conversion catalyst. In one layered composite, the composite is located in at least one channel of a honeycomb monolith. The innermost layer (proximate to the established flows) comprises the oxygen storage material. The outermost layer comprises hydrocarbon conversion catalyst.

IV. Oxidative Coupling Catalysts and Oxydehydrogenation Catalysts

The hydrocarbon conversion catalyst is effective in converting alkane (e.g., $C_{5-}$ alkane, such as methane) in the presence of oxygen released form the oxygen storage material to produce a first reaction mixture comprising a $C_{2+}$ composition (e.g., $C_2$ to $C_4$ hydrocarbon, such as $C_2$ to $C_4$ alkane and/or $C_2$ to $C_4$ olefin, particularly ethane and ethylene). Suitable hydrocarbon conversion catalysts include oxydehydrogenation catalysts and oxidative coupling catalysts, such as metal oxide hydrocarbon conversion catalysts useful in oxydehydrogenation and oxidative coupling reactions. The metal oxide catalysts also include mixed metal oxide catalysts, meaning that there may be more than one metal element in the oxide catalyst. Particularly useful metal oxide catalysts are metal oxide catalysts effective in catalytically converting alkane (e.g., methane) to $C_{2+}$ compositions (e.g., ethane and/or ethylene), particularly $C_{2+}$ olefin (e.g., ethylene).

The hydrocarbon conversion catalyst can include oxydehydrogenation catalysts and oxidative coupling catalysts, such as metal oxide hydrocarbon conversion catalysts useful in oxydehydrogenation and oxidative coupling reactions. The metal oxide catalysts also include mixed metal oxide catalysts, meaning that there may be more than one metal element in the oxide catalyst. Particularly useful metal oxide catalysts are metal oxide catalysts effective in catalytically converting alkane (e.g., methane) to $C_{2+}$ olefin (e.g., ethylene).

An effective metal oxide catalyst can include at least one base metal of IUPAC Group 2, Group 3, Group 7, Group 8, Group 9, Group 14, Group 15 and the lanthanide series of metals. The metal oxide catalyst can additionally include at least one Group 1 metal. Examples of each these metals are shown in the PERIODIC CHART OF THE ELEMENTS, The Merck Index, 12th Ed., Merck & Co., Inc., 1996 ("Periodic Table").

Examples of Group 1 metals include Li, Na, K, Rb, Cs and Fr. Li, Na, K, Rb and Cs represent more common Group 1 metals.

Examples of Group 2 metals include Be, Mg, Ca, Sr, Ba and Ra. Mg, Ca, Sr and Ba are more common Group 2 metals.

Examples of Group 3 metals include Sc, Y, La and Ac. La is an example of a particularly common Group 3 metal.

Examples of Group 7 metals include Mn and Re. Mn is an example of a particularly common Group 7 metal.

Examples of Group 8 metals include Fe, Ru and Os. Fe is an example of particularly common Group 8 metal.

Examples of Group 9 metals include Co, Rh and Ir. Co is an example of particularly common Group 9 metal.

Examples of Group 14 metals include Sn and Pb. Pb is an example of a particularly common Group 14 metal.

An example of a Group 15 metal includes Bi.

Examples of the lanthanide series of metals include Ce, Pr, Nd, Sm, Eu, Gd, Tb, Dy, Ho, Er, Tm, Yb and Lu. Sm, Gd, Ho, and Yb are more common lanthanide metals.

Specific examples of oxidative coupling catalysts include those listed in U.S. Pat. No. 6,096,934. Such catalysts include lithium supported on magnesium oxide where the lithium is present in either the hydroxide or oxide form; bismuth supported on calcium oxide where the bismuth is present in either the hydroxide or oxide form; lithium supported on calcium oxide where the lithium is present in either the hydroxide or oxide form; cerium supported on magnesium oxide where the cerium is present in either the hydroxide or oxide form; nickel and lanthanum supported on magnesium oxide where the lanthanum is present in either the hydroxide or oxide form and the nickel is present in the metallic form; and lithium supported on lanthanum oxide where the lithium is present in either the hydroxide or oxide form; or any other metal or metal oxide or hydroxide catalyst promoted with a Group 1, 2, or lanthanide series element present in an oxide or hydroxide form.

U.S. Pat. No. 5,245,124 discloses an order of oxidative coupling catalysts first reported by Y. A. Amenomiya et al. in "Conversion of Methane by Oxidative Coupling," report to CANMET, Energy, Mines and Resources, Ottawa, Canada. The rating of catalysts is listed as follows: $Li/Sm_2O_3$>Na/CaO>K/CaO>$LaAl_2O_3$>$Sm_2O_3$>Li/CaO>PbO>$Bi_2O_3$>$Ho_2O_3$>$Gd_2O_3$>Li/MgO>Li/CaO~$Yb_2O_3$>$Y_2O_3$Na/MgO~CaO>MgO. Additives to the catalysts include Ba, Li, Sr, Pb, K, Mg, Ca, Na, and Sb.

Perovskites of the structure $A_2B_2C_3O_{10}$ are also useful as catalysts for the oxidative coupling and/or oxydehydrogenation of lower alkane to heavier hydrocarbons. A is alkali metal; B is lanthanum or a lanthanide element, for example, cerium, neodymium, samarium, praseodymium, gadolinium or dysprosium; and C is titanium. A particular example is shown in U.S. Pat. No. 5,026,945, in which the perovskite is represented by the formula $A_xLn_yTi_zO_{10}$, wherein A is one or more alkali metal; Ln is one or more of lanthanum, cerium, neodymium, samarium, praseodymium, gadolinium and dysprosium; x is about 2; y is about 2; and z is about 3.

The catalysts can be incorporated with the thermal mass of the reactor in a configuration in which (i) hydrocarbon reactant flowing through the flow-through reactor and (ii) stored oxygen released from the oxygen storage material react in the presence of the hydrocarbon conversion catalyst to convert alkane (e.g., methane) in the hydrocarbon reactant to $C_{2+}$ hydrocarbon (e.g., ethane and/or ethylene). The hydrocarbon conversion catalyst can be arranged along with one or more of the thermal masses or segments of a thermal mass of the reactor to transfer heat to the hydrocarbon reactant as it passes through the flow-through reactor. It has been observed that some of the materials that are suitable for use as the specified hydrocarbon conversion catalyst are also suitable for use as oxygen storage material. Such "dual-use" materials include those hydrocarbon conversion catalysts that (i) have two or more oxidation states, and (ii) are capable of oxygen uptake and release under the specified oxygen transfer conditions without substantial decomposition. Perovskite is an example of a "dual use" material.

V. Reactor Feed Compositions

A first feed stream to the flow-through reactor includes oxidant (optionally as a heating fluid or a component thereof), which can be passed to the flow-through reactor at a first time interval. A second feed stream to the flow-through reactor includes hydrocarbon reactant, which can be passed to the flow-through reactor at a second time interval.

When the oxidant is contained in heating fluid, the heating fluid can be any oxygen-containing fluid that is (i) capable of transferring oxygen from the heating fluid to the oxygen storage material for storage with the oxygen storage material and (ii) capable of transferring heat to the flow-through reactor, such as transferring heat to the thermal mass of a flow-through reactor. The transfer can be through direct or indirect heat transfer between the heating fluid and the thermal mass. The heat transfer can include one or more exothermal reactions, which produces heat that is transferred to the thermal mass.

The oxidant typically comprises one or more fluids which yield oxygen for the specified transfer/storage under the specified oxygen transfer/storage conditions. Typically, the oxidant includes one or more of molecular oxygen ($O_2$), $O_2^-$, $O_2^=$, ionized oxygen atoms, nitrogen oxides such as $N_2O$, etc. Oxidant is typically in the vapor phase at the specified hydrocarbon conversion conditions, but this is not required, and in certain aspects liquid and/or solid oxidant can be used. The oxidant can comprise $O_2$, e.g., ≥90% $O_2$ (molar basis, per mole of oxidant), such as, ≥99%. For example, the oxidant can comprise $O_2$ in air, or $O_2$ obtained or derived from air, e.g., by separation. The oxidant can comprise (or consist essentially of, or consist of) $O_2$ in air. When the oxidant comprises $O_2$ in air, the total feed during the oxidant transfer/storage interval generally comprises at least a portion of the air's molecular nitrogen as diluent. In other words, when the oxidant comprises molecular oxygen in air, other gasses in the air, such as molecular nitrogen, are considered to be diluent, and are not considered to be part of the oxidant.

In alternative embodiments, the heating fluid further comprises hydrocarbon fuel. Hydrocarbon fuel can be considered any hydrocarbon or hydrocarbon mixture effective in carrying out a combustion reaction to release heat and produce combustion products such as carbon monoxide, carbon dioxide, water and combinations thereof. The heating fluid preferably contains oxygen from the oxidant at a stoichiometric excess for substantially complete combustion with the hydrocarbon fuel, and at least a portion of the oxidant (i.e., oxygen) is stored with the oxygen storage material. Examples of suitable hydrocarbon fuels include natural gas mixtures, other petroleum alkane-containing mixtures, petroleum distillates, kerosene, jet fuel, fuel oil, heating oil, diesel fuel and gas oil, gasoline, and alcohols. The hydrocarbon fuel can be selected from among the same compositions as the hydrocarbon reactant. For example, the hydrocarbon fuel can be of the same composition as the hydrocarbon reactant and/or can be obtained from the same source.

In certain embodiments, the oxidant comprises molecular oxygen ($O_2$). For example, the oxidant can comprise ≥90.0 wt. % of $O_2$, e.g., ≥99.0 wt. % of $O_2$, based on total weight of the oxidant. The $O_2$ can be $O_2$ in air, or $O_2$ obtained or derived from air, e.g., by separation. Nitrogen obtained or derived from air can be utilized as a feed mixture diluent.

In certain embodiments, the hydrocarbon reactant comprises alkane, e.g., $C_{5-}$ alkane. The alkane can comprise one or more $C_1$ to $C_5$ linear, iso, and cyclo alkanes. Specific examples include methane, ethane, propane, butane and pentane. Particular examples include methane, ethane and propane, with methane being a preferred alkane.

The hydrocarbon reactant can comprise ≥80 wt. % alkane, or ≥85 wt. % alkane, or ≥90 wt. % alkene, based on total weight of the hydrocarbon reactant. For example, the hydrocarbon reactant can comprise ≥80 wt. % methane, or ≥85 wt. % methane, or ≥90 wt. % methane, based on total weight of the hydrocarbon reactant, with the remainder of the hydrocarbon in the hydrocarbon reactant comprising one or more of $C_2$ to $C_5$ linear, iso, and cyclo alkane. Such a hydrocarbon reactant can also be used as the hydrocarbon fuel component of a heating fluid, if desired.

The feed streams (e.g., the heating fluid and/or the hydrocarbon reactant) can be diluted, e.g., with one or more diluents such as one or more inert materials. For example, the feed streams can be diluted with essentially inert fluid. Examples of inert fluid include steam, nitrogen, carbon dioxide or other fluids that are substantially unreactive with the hydrocarbon in the feed streams. When diluted, the diluent can provide from 5 wt. % to 80 wt. % of the feed streams, or from 10 wt. % to 50 wt. %, based on total weight of the feed streams. Dilution can be carried out by adding diluent to one or more of the reactant (alkane component of the feed stream), the oxidant, or the mixed reactant, and oxidant.

VI. $C_2$ Selective Sorbent

The flow-through reactor can contain $C_2$ selective sorbent, e.g., for removing ethylene and/or ethane from the reaction mixture's $C_{2+}$ composition. For example, $C_2$ selective sorbent can be located proximate to thermal mass (or a segment thereof) in the flow-through reactor, e.g., proximate to or as a component of (i) the hydrocarbon conversion catalyst, (ii) the oxygen storage material, and (iii) any additional thermal mass. For example, the $C_2$ selective sorbent can be included as one or more portions or sections of the thermal mass, over which the gasses pass. For example, the $C_2$ selective sorbent can be arranged at a surface of one or more sections of the thermal mass, over which reaction mixture passes.

In an alternative optional embodiment, the $C_2$-selective sorbent can be included in external arrangement with the reactor. For example, the $C_2$ selective sorbent can be included in a $C_2$ selective sorption system, configured in fluid communication with an exit aperture of the flow-through reactor for receiving at least a portion of the catalytically converted reaction mixture.

Selective removal of one or more desired $C_2$ compositions can be carried out without having to rely on cryogenic processes by using a $C_2$ selective sorbent. The $C_2$ selective sorbent is preferably configured to selectively remove or extract at least one $C_2$ compound from a gas stream as the gas stream flows past or through the $C_2$ selective sorbent.

As used herein, a sorbent is considered a generic term, which includes "absorbent" and "adsorbent." An absorbent is a material that absorbs or incorporates a substance into the body of the absorbent material, which can also be referred to as absorption. For example, an absorbent can be used to absorb or attract or remove or extract a substance from another substance or from a mixture of substances. An adsorbent is a material that adsorbs or attracts a substance to the surface of the sorbent material, which can also be referred to as adsorption. For example, an adsorbent can be used to adsorb or attract or remove or extract a substance from another substance or from a mixture of substances.

The $C_2$ selective sorbent is effective in removing or selectively sorbing one or more $C_2$ compounds from a hydrocarbon-containing composition. Alternatively or in addition, the sorbent can be effective in removing or selectively sorbing one or more olefin compounds from a hydrocarbon-containing composition. In particular, the sorbent can be effective in selectively sorbing or removing at least one compound selected from the group consisting of ethane, ethylene and acetylene. In some cases, the sorbent can selective for one of ethane, ethylene and acetylene. For example, a sorbent selective for ethylene over ethane and acetylene can be used. Alternatively, the sorbent can selective for two of ethane, ethylene and acetylene. Alternatively, the sorbent can selective for each of ethane, ethylene and acetylene.

In cases in which a first sorbent is used to sorb at least two of ethane, ethylene and acetylene, or each of ethane, ethylene and acetylene, a second sorbent, can be used. The second sorbent typically comprises at least one olefin-selective sorbent, which can be used in a subsequent step to separate one of the $C_2$ compounds sorbed by the first sorbent. For example, in a first step a sorbent selective for selectively separating ethane and ethylene from methane can be used (a $C_2$ selective sorbent), followed by a second sorption step in which a sorbent selective for separating ethylene can be used (an olefin-selective sorbent).

$C_2$ selective sorbents typically comprise at least one solid composition that is effective in selectively removing at least one $C_2$ component from a gas stream containing one or more $C_2$ compositions as the gas stream passes across or through the sorbent. The particular type of sorbent to be used can depend on the particular nature of the gases to be separated.

A kinetic separation separates by differences in diffusion and/or sorption rates through the sorbent; the differences in diffusion rates may be caused by chemoselectivity, shape selectivity or a combination of both. Kinetic separations are different than thermodynamics separations. In a thermodynamic separation, sufficient time is allowed for the gases to equilibrate with the sorbent. However, in a kinetic separation, equilibrium is not achieved (e.g., by operating at higher rates per volume of sorbent, or by shortening the bed). Moreover, kinetic adsorbents discriminate amongst species by significant differences in the speed of diffusion and/or adsorption of ethylene compared to ethane, regardless of the respective species' equilibrium capacities/selectivities. For example, in a situation in which ethylene is the desired sorbate, a sorbent can be used that is particularly selective for ethylene at a pre-determined temperature. In a particular embodiment, the sorbent sorbs ethylene from the reaction mixture under kinetic conditions, wherein the sorbent is one that is selective for removing ethylene from a $C_{2+}$ gas stream under kinetic conditions at a temperature region within or below the desired temperature range of the specified hydrocarbon conversion reaction.

In certain embodiments, the sorbent comprises $C_2$ selective sorbent having a selectivity for sorbing the desired $C_2$ composition over sorbing of methane that is greater than 5. Alternatively, the adsorbent for removing at least one of the $C_2$ compositions is comprised of a $C_2$ selective adsorption material having an adsorptive loading ratio for the desired $C_2$ composition over methane of at least 10, or at least 15, or at least 20. Examples of such materials include zeolitic imidazolate framework materials, such as ZIF-7, ZIF-9 and ZIF-1 as described in greater detail in U.S. Pat. No. 8,192,709.

The adsorptive loading ratio is a property for a specific adsorbate-adsorbent pair, at given conditions of pressure and temperature. This ratio is defined herein as a unitless quantity that is equal to the adsorption loading (in mmole/g) for the first component divided by the adsorption loading (in mmole/g) for the second component for a specific adsorbent material at a specific pressure and temperature. The adsorption loading for the desired $C_2$ composition on a particular adsorbent can be carried out as also described in U.S. Pat. No. 8,192,709, the description of which is incorporated herein by reference.

In certain embodiments, the $C_2$ selective sorbent can have a $C_2$:methane selectivity >1. For example, the $C_2$ selective sorbent can retain >50% [ethylene+ethane] and <50% methane. Preferably, the $C_2$ selective sorbent has a $C_2$:methane selectivity >5 (i.e., retains >83% [ethylene+ethane]). More preferably, the $C_2$ selective sorbent has a $C_2$:methane selectivity >99 (i.e., retains >99% [ethylene+ethane]); even more preferably, a $C_2$:methane selectivity >999 (i.e., retains >99.9% [ethylene+ethane]); even more preferably, a $C_2$:methane selectivity >9999 (i.e., retains >99.99% [ethylene+ethane]).

In additional embodiments, the $C_2$ selective sorbent can have an ethylene:ethane selectivity >1 (i.e., retains >50% ethylene, <50% ethane). Preferably, the $C_2$ selective sorbent can has an ethylene:ethane selectivity >5 (i.e., retains >83% ethylene). More preferably, the $C_2$ selective sorbent has an ethylene:ethane selectivity >99 (i.e., retains >99% ethylene); even more preferably >999 (i.e., retains >99.9% ethylene); even more an ethylene:ethane selectivity >9999 (i.e., retains >99.99% ethylene).

In certain aspects, the olefin-selective sorbents include high surface area, porous materials which have been treated with transition metal species capable of π-complexation with olefins. In particular, the double bond of the olefin can form π-complexes with certain transition metals, bringing about a difference in adsorption affinity between olefin and paraffin compositions. The π-complex is formed by the donation of π-electrons of the olefin to the empty σ-orbital of a transition metal and the back-donation of d-electrons of the transition metal to the π*-orbitals of the olefin. Optionally, the olefin-selective sorbents have an electron affinity ≥1.0 ev, e.g., ≥5.0 ev, such as ≥7.0 ev. Metals satisfying one or both of these criteria are those from groups IA through VIIIA, IB and IIB on the periodic table and their combinations. These metals may be extra-framework (e.g., ion exchanged or as metal clusters) or may be part of the framework of the adsorbent (by isomorphic substitution).

Group 9 transition metals are examples of transition metals that have a relatively high degree of π-complexation with olefins. Specific examples of Group 9 transition metals include copper and silver, particularly in their salt form. Such sorbents are described in U.S. Pat. No. 4,917,711, which describes the use of supports such as zeolite 4A, zeolite X, zeolite Y, alumina and silica, each treated with a copper salt, to selectively remove carbon monoxide and/or olefins from a gaseous mixture containing saturated hydrocarbons (i.e. paraffins) such as ethane and propane.

In certain embodiments, the olefin selective sorbent can be comprised of a molecular sieve substrate material having an average pore size that selectively excludes ethane from entering the pores of the sorbent, but allows ethylene to enter. For example, the olefin selective sorbent can have an average pore size of not greater than 4.4 angstroms, or not greater than 4.3 angstroms, or not greater than 4.2 angstroms.

In particular embodiments, the olefin selective sorbent can be comprised of a small pore molecular sieve. As an example, a small pore molecular sieve can comprise at least one set of pores of substantially uniform size extending through the molecular sieve, wherein geometric mean of the cross-sectional dimensions of each of the pores is less than or equal to 4.4 Å. Suitable molecular sieves comprise zeolites, silico-alumino-phosphates (SAPOs), alumino-phosphates (AlPOs), metal organic frameworks (MOFs), zeolite imidazoline frameworks (ZIFs) and polyaromatic frameworks (PAFs). Examples of suitable molecular sieves include materials having the framework types CHA, WEN, ABW, PHI, IHO, GIS, LOV, MON, AEI, POU, ATV, MFS, DDR, ATN, CHI, FER, LTA, LEV, ROG, DAC, ERI and ATT (see "Atlas of Zeolite Framework Types", eds. Ch. Baerlocher, L. B. McCusker, D. H. Olson, Elsevier, Sixth Revised Edition, 2007, which is hereby incorporated by reference). For example, ATT framework type molecular sieves have two sets pores, each defined by 8-ring channels, extending through the molecular sieve, wherein the pores of one set having cross-sectional dimensions of 4.2 Å×4.6 Å (geometric mean 4.4 Å) and the pores of the other set having cross-sectional dimensions of 3.8 Å×3.8 Å (geometric mean 3.8 Å). Thus, the geometric mean of the cross-sectional dimensions of all the pores defined by these 8-ring channels in ATT material is less than or equal to 4.4 Å.

The $C_2$ selective sorbent typically has a surface area of ≥50 $m^2/g$, such as ≥100 $m^2/g$.

VII. $C_2$-Selective Sorption Process and System

The $C_2$-selective sorbent has an ultimate capacity for sorbing the sorbate (e.g., the $C_2$ composition) from the reaction mixture produced from the oxidative coupling reactions and/or oxydehydrogenation reactions. Exposing the reaction mixture to at least one $C_2$ selective sorbent results in the selective sorption of at least a portion of the reaction mixture's $C_2$ composition, producing a $C_2$ lean mixture.

During the sorption process, the appearance of an increased amount of the $C_2$ composition in the $C_2$ lean mixture can be an indication that the one $C_2$-selective sorbent is approaching the ultimate capacity. The appearance of an increased amount of the $C_2$ composition in the $C_2$ lean mixture can also be referred as "break-through." At a predetermined time of break-through, the passing of the reaction mixture to the $C_2$ selective sorbent can be lessened or discontinued, and the sorbed olefin can be desorbed from the $C_2$ selective sorbent.

Typically, the $C_2$ composition is desorbed from the one $C_2$ selective sorbent in order to (i) regenerate the one $C_2$-selective sorbent (to restore capacity for sorbing the reaction mixture's $C_2$ composition) and (ii) to recover the desorbed $C_2$ composition. Conventional sorbent regeneration conditions are suitable. Desorption be carried out by a reduction in temperature, pressure or both.

Optionally, a sweep fluid can be used to assist in desorbing the $C_2$ composition. Typical sweep fluids include relatively inert liquids and vapors, especially those which are relatively easy to separate from the desorbed $C_2$ composition. Steam and/or molecular nitrogen are suitable sweep fluids. $C_2$ unsaturates can be separated from the $C_2$ composition, e.g., for storage and/or further processing, such as the polymerization of ethylene obtained from the $C_2$ composition.

In one embodiment, selective separation or sorption of the sorbate, i.e., sorption of the $C_2$ composition, is carried out at a temperature region below that of the hydrocarbon conversion reaction. For example, the sorbent can be located in a sorption region or zone in which the sorption zone is downstream of the reaction zone, and the sorption zone is at an average zone temperature lower than that of the average zone temperature within the reaction zone. As an example, the sorption zone can be at an average zone temperature of at least 50° C., or at least 100° C., or at least 200° C., or at least 400° C. lower than the average zone temperature within the reaction zone. More particularly, selective separation of the $C_2$ composition, such as from the $C_2$ lean mixture and/or the $CO_2$ lean reaction mixture, can be carried out at a temperature of ≥50° C. and below that of the average zone temperature within the reaction zone.

In one embodiment, desorption of the sorbate can be carried out at an average sorption zone temperature of from 50° C. to 400° C. lower than the average zone temperature of the reaction zone. Alternatively, desorption of the sorbate can be carried out at an average zone temperature of from 100° C. to 300° C. lower than the average zone temperature of the reaction zone.

Desorption of the sorbate can also be carried out at an average temperature above that for sorption of the sorbate. For example, desorption of the sorbate can also be carried out at an average temperature of at least 4° C., or at least 5° C., or at least 6° C. above that for sorption of the sorbate. In one embodiment, desorption of the sorbate is carried out at 4° C. to 200° C. above that for sorption of the sorbate.

In a case in which the sorbate includes at least one of ethylene and ethane, sorption can be carried out at a temperature range of from 50° C. to 400° C. Alternatively, in a case in which the sorbate includes at least one of ethylene and ethane, sorption can be carried out at a temperature range of from 100° C. to 300° C.

Pressure at which sorption is carried out can be greater than the pressure range of the reaction zone. As a practical matter, the pressure of the sorption zone can be ≥100 psig (489 kPag), such as from 100 psig (489 kPa) to 500 psig (3447 kPag).

In certain embodiments, desorption of the sorbate can be carried out at an average pressure below that for sorption of the sorbate. For example, desorption of the sorbate can be carried out at an average pressure of from >0 psia (0 kPa) and from 1 psia (6.9 kPa) to 485 psia (3344 kPa) below that for sorption of the sorbate.

The adsorbents for selectively removing the desired $C_2$ composition can be utilized in a swing adsorption process or system. The general terms "swing adsorption process" and "swing adsorption system" as used herein shall be taken to include Pressure Swing Adsorption ("PSA"), Temperature Swing Adsorption ("TSA"), Pressure Purge Displacement Processes ("PPSA"), Rapid Cycle Pressure Swing Adsorption ("RCPSA"), Rapid Cycle Temperature Swing Adsorption ("RCTSA"), Rapid Cycle Pressure Purge Swing Absorption ("RCPPSA") as well as combinations of these swing adsorption processes. Alternatively, a simulated moving-bed chromatography separation may be used. In a preferred embodiment, the stream to be separated is fed to the process in a substantially gaseous state.

VIII. Examples

Example 1

With Reference to FIGS. 1A and 1B

Certain embodiments of the invention are depicted in FIGS. 1A and 1B. FIG. 1A illustrates a flow-through reactor, for example a catalytic reverse-flow reactor having a first region (Region 1) and a second region (Region 2), with the first and second regions comprising thermal mass.

The invention, however, is not limited to catalytic reverse-flow reactors having two regions, and the FIG. 1A description is not intended to foreclose other configurations of thermal mass. For example, the thermal mass material may be coupled together as a continuous mass in a single region or coupled in a series arrangement having more than two regions. As another example, the thermal mass can be a continuous mass of a refractory material having catalytic functionality (i.e., includes the hydrocarbon conversion catalyst) and oxygen-storage functionality (i.e., includes the oxygen storage material). In such a case, the thermal mass would be a bi-functional thermal mass.

The terms first and second thermal mass segments are used for convenience in FIG. 1A to particularly describe the heating and cooling of the regions of the thermal mass as the catalytic reaction progresses through the flow of the feeds. The reaction being carried out results in the transfer of heat in a manner that is effective in the continuous catalytic conversion of alkane in the hydrocarbon reactant feed to produce a reaction mixture comprising $C_{2+}$ compositions, particularly $C_{2+}$ olefins.

The reactor in FIG. 1A includes a continuous thermal mass segment, which is represented as a first thermal mass segment M1 and a second thermal mass segment M2, with the thermal mass including a Reaction Zone C. The Reaction Zone C comprises at least one oxygen storage material and at least one hydrocarbon conversion catalyst, which can be incorporated on or in either or both of the thermal mass segments M1 and M2 of the Reaction Zone C. For example, all of the oxygen storage material and hydrocarbon conversion catalyst can be incorporated in or on either thermal mass segment M1 or thermal mass segment M2 or a portion of the oxygen storage material and/or hydrocarbon conversion catalyst can be incorporated in or on both thermal mass segments M1 and M2.

In an embodiment, at least a portion of the oxygen storage material and at least a portion of the catalyst in the Reaction Zone C can be deposited on or in the first thermal mass segment M1 and/or the second thermal mass segment M2. The oxygen storage material and catalyst in the Reaction Zone C can overlap both Region 1 and Region 2. However, the oxygen storage material and hydrocarbon conversion catalyst can be completely located in either Region 1 or Region 2, and/or in a region located between Regions 1 and 2. The oxygen storage material and hydrocarbon conversion catalyst can be part of or attached to the thermal mass material of Region 1, Region 2, or both. Optionally, the oxygen storage material and catalyst are located in a defined sub-region of the first and/or second thermal mass segments, the sub-regions being proximate to the center of the reactor as shown in FIG. 1A.

In a particular embodiment, (i) a first portion of a hydrocarbon conversion catalyst, e.g., ≥10.0% (weight basis) of the hydrocarbon conversion catalyst and ≥10.0% (weight basis) of a first oxygen storage material can be located on (or in) the first thermal mass segment M1, such as in a region proximate to a downstream end of the first thermal mass segment M1 (downstream being with respect to the flow of feeds); and (ii) a second portion of the hydrocarbon conversion catalyst, e.g., ≥10.0% (weight basis) of the hydrocarbon conversion catalyst can be located on (or in) the second thermal mass segment M2 and ≥10.0% (weight basis) of a second oxygen storage material can be located on (or in) the second thermal mass segment M2, such as in a region proximate to a downstream end of the second thermal mass segment M2 (downstream being with respect to the flow of the feeds). The first and second oxygen storage materials can be the same or different.

FIG. 1B is a characterization of a cross-sectional enlargement of the Reaction Zone C. "M" of FIG. 1B refers to a metal center, representative of at least one oxygen storage material. "O" of FIG. 1B refers to an oxidant such as oxygen, which has been stored in the Reaction Zone C from a first process step in which heating fluid comprising an oxidant is flowed through the reactor.

As seen in FIG. 1B oxygen from the oxidant can be stored in a portion of the thermal mass of the reaction zone containing oxygen storage material M. As the oxidant is flowed through the reactor, at least a portion of the oxidant (i.e., oxygen) is stored with the oxygen storage material. The oxygen can migrate from the surface S of the thermal mass toward a more central region of the thermal mass, becoming more deeply embedded in the thermal mass. As flow of oxidant continues, the storage of oxygen can reach a maximum or saturation-type level. The oxygen at the surface S of the thermal mass is more loosely bound to the oxygen storage material than the oxygen at the oxygen embedded further inwardly. Thus, the surface oxygen (depicted as the O's above the dotted line of FIG. 1B) is more easily released. This can be a particular advantage in heat balance at the beginning of a reaction process. For example, excess oxygen at the surface means that the reaction process can be more easily initiated. Thus, less energy can be used to carry out the overall reaction process.

As the hydrocarbon reactant is flowed through the reactor, the stored oxygen is released, catalytically reacting with the alkane in the hydrocarbon reactant to produce a reaction mixture comprising a $C_{2+}$ composition.

With reference to FIG. 1A, during a first step of the process for producing the $C_{2+}$ composition, or during a first time interval, heating fluid comprising an oxidant is passed through the flow-through reactor to heat the thermal mass in a forward direction, as shown by the direction of the arrow pointing toward M1. Oxygen from the oxidant is stored with the oxygen storage material in Reaction Zone C as the oxidant is passed through the reactor, with heat produced during the oxygen storage being transferred to the thermal mass. Storage of the oxygen with the oxygen storage material can involve or include at least one exothermal reaction, causing heat to be generated, with heat transfer being carried out through storage of the oxygen with the oxygen storage material in Reaction Zone C. The heating fluid can further comprise a hydrocarbon fuel.

Following the heating of the thermal mass, i.e., during a second time interval, a hydrocarbon reactant comprising ≥10.0 wt. % alkane (e.g., methane), based on total weight of the hydrocarbon reactant, is passed through the flow-through reactor. As the reactant flows through the reactor, stored oxygen is released from the oxygen storage material. The hydrocarbon reactant contacts the heated thermal mass, causing the reactant to heat. As the heated reactant flows through the reactor, stored oxygen is released from the oxygen storage material. Contact of the heated hydrocarbon reactant and released oxygen in the presence of the hydrocarbon conversion catalyst in Reaction Zone C produces a catalytic conversion of at least a portion of the hydrocarbon reactant's alkane in the Reaction Zone C, producing a reaction mixture comprising the $C_{2+}$ composition. The reaction mixture can be conducted away from the reactor for further processing.

The heating fluid and hydrocarbon reactant is flowed in the same direction (i.e., a forward direction as shown by the arrow of FIG. 1A) during a subsequent (and substantially separate) time interval. For example, the heating fluid can be flowed in a forward direction (namely in the direction of the arrow pointing at M1 in FIG. 1A) through the flow-through reactor, during a first time interval. During a second or subsequent time interval, the hydrocarbon reactant also can be flowed in the forward direction through the flow-through reactor.

The flow-through reactor of FIG. 1A can be operated as a reverse-flow reactor, with the oxygen-storage step being carried out in a first time interval and the catalytic conversion step being carried out in a second time interval. When the process is carried out in a reverse-flow arrangement, heating fluid and hydrocarbon reactant are flowed in opposite directions through the reverse-flow reactor during separate time intervals.

As shown in FIG. 1A, the heating fluid is flowed in a first or forward direction through the flow-through reactor, during a first time interval. When the flow-through reactor is operated in a reverse-flow arrangement, during a second or subsequent time interval, the hydrocarbon reactant is flowed in a second or reverse direction of the arrow shown in FIG. 1A.

The first and second time intervals, as generally described according to the exemplary scheme shown in FIG. 1A, can be substantially non-overlapping intervals. Each of the first and second time intervals can be, independently, an interval having a duration in the range of from about 0.5 seconds to about 15 seconds. The interval between the first and second time intervals (the "dead-time", which represents the interval of time it takes to reverse flow of the feed mixtures) is preferably as short as possible so that the reverse flow cycle can be as rapid as possible. From a practical standpoint, the dead-time should be, e.g., ≤ than 0.5 seconds, such as in a range of from about 0.01 seconds to about 0.5 seconds. Upon completion of the second time interval, the intervals can be repeated. That is, the flow shown in FIG. 1A can be reinitiated and followed by subsequent re-initiation of the flow shown in FIG. 1A.

A sweep fluid can be passed through the catalytic reverse-flow reactor after the oxygen storage step and/or after the catalytic conversion step. For example, a sweep fluid can be used during a third time interval to remove at least a portion of a combustion gas and/or unconverted heating fluid that might remain within the reactor between the first time interval and the second time interval. The sweep fluid can be passed in the forward direction or the reverse direction. The sweep fluid can be an inert fluid. Examples of inert fluids include, but are not limited to, steam, molecular nitrogen, carbon dioxide or other fluids that are substantially unreactive with any hydrocarbon that may be present in the reactor.

As a particular example in which the heating fluid further comprises a hydrocarbon fuel, the heating fluid can be passed through the flow-through reactor, at a first time interval, under combustion conditions to produce a combustion gas, with heat being transferred from the combustion gas to the thermal mass. After the first time interval, i.e., during a second time interval, a sweep fluid can be passed through the flow-through reactor to remove at least a portion the combustion gas.

As another example, during a third time interval, a hydrocarbon reactant can be passed through the flow-through reactor to contact the thermal mass heated during the first time interval. The heated thermal mass can heat the hydrocarbon reactant, and the heated hydrocarbon reactant can be catalytically converted in the presence of the hydrocarbon conversion catalyst the stored oxygen to a reaction mixture comprising a $C_{2+}$ composition. After the third time interval, i.e., during a fourth time interval, additional sweep fluid can be passed through the flow-through reactor to remove at least a portion the reaction mixture.

In the exemplary embodiment shown in FIGS. 1A and 1B, the oxidant can comprise $O_2$ in air. The hydrocarbon reactant can comprise ≥80 wt. % methane.

In another aspect (not shown), at least a portion of the separated $C_{2+}$ composition can be polymerized. For example, in certain embodiments in which the separated $C_{2+}$ composition comprises olefin such as ethylene and/or propylene, the ethylene and/or propylene can be polymerized, e.g., to produce a polyethylene and/or polypropylene compositions.

Example 2

Figure 2:
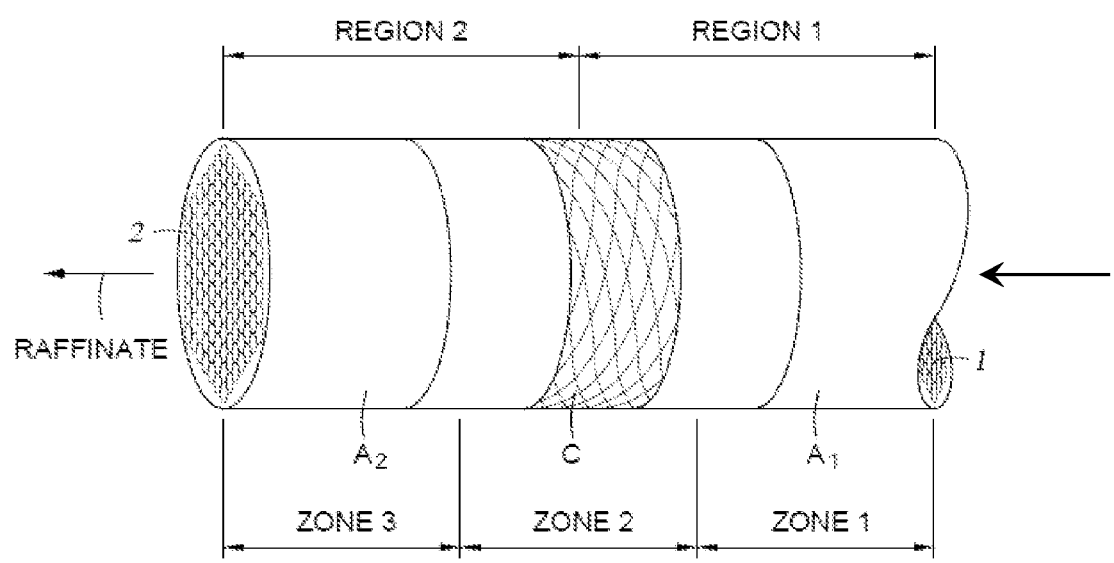
FIG. 2 is an example of a flow-through reactor, which includes first and second thermal mass segments M1 and M2, a Reaction Zone C, and sorption zones A2, A1.

With Respect to FIG. 2

Another embodiment of a basic flow-through reactor system according to the present invention is depicted in FIG. 2, illustrating a flow-through reactor including two regions: a first region (Region 1) and a second region (Region 2), in which the Region 1 and Region 2 can be considered to comprise a first thermal mass segment and a second thermal mass segment.

The embodiment depicted in FIG. 2 further includes three zones, Zones 1-3, in which Zone 1 includes a sorption Zone A1, Zone 2 includes a Reaction Zone C, and Zone 3 includes a sorption Zone A2. A first $C_2$ selective sorbent can be included in the sorption Zone A1. At least one oxygen storage material and at least one hydrocarbon conversion catalyst, as described in Example 1 according to FIG. 1A, can be included in the Reaction Zone C. A second $C_2$ selective sorbent can be included in the sorption zone A2. The first and second $C_2$ selective sorbents can be the same or different. The $C_2$ selective sorbents can be configured to selectively remove olefins from the flowing streams, as previously described.

The catalytic Reaction Zone C shown in FIG. 1A and in Zone 2 of FIG. 2 can include a first and/or second oxygen storage material, as previously described, and first and/or second portions of the hydrocarbon conversion catalyst, as previously described.

FIG. 2 further depicts a step of separating $C_2$ compositions from the reaction mixture to form a raffinate stream, which exits the flow-through reactor. For example, a hydrocarbon reactant, as described with regard to Example 1 and FIG. 1A can be injected into the inlet 1 of the first thermal mass segment of Region 1. The hydrocarbon is then passed through or across the first thermal mass segment of Region 1, which has been previously heated in a previous step through introduction of oxidant, as also described with regard to Example 1 and FIG. 1A.

The reaction in the Reaction Zone C is carried out through release of oxidant previously stored with the oxygen storage material as the hydrocarbon passes through the Reaction Zone C, as previously described in Example 1. Contact of oxidant and hydrocarbon in the hydrocarbon reactant converts hydrocarbon to olefin, preferably by exothermic reaction, to produce the reaction mixture comprising $C_{2+}$ olefin, produced by the alkane conversion, and any unconverted portion of the hydrocarbon reactant. Heat is transferred from the reaction mixture to the second thermal mass segment as the reaction mixture flows toward the outlet 2. As the reaction mixture passes across the sorption zone A2, $C_2$ selective sorbent present in the sorption zone A2 sorbs at least a portion of the third mixture's $C_{2+}$ composition, and at least a portion of the raffinate in the reaction mixture is conducted away from the reverse flow-reactor by way of the exit 2.

A desorption step in which sweep fluid is used to desorb the $C_{2+}$ composition from $C_2$ selective sorbent in sorption zone A2, sorption zone A1, or both, can follow the conversion step. For example, a sweep fluid can be passed through the exit 2 in reverse flow relative to the hydrocarbon reactant feed. Heat from the sweep fluid can be transferred to the second thermal mass segment of Region 2, with the flow of cooled sweep fluid being used to displace or desorb the $C_{2+}$ composition from the $C_2$ selective sorbent in sorption zone A2, the sorption zone A1, or both. The sweep fluid and the desorbed $C_{2+}$ composition exit the reactor through the inlet 1. Desorption can also be carried out in forward flow direction, using the sweep fluid. The sweep fluid can comprise ≥50.0 wt. % steam, based on total weight of the first sweep fluid.

At least a portion of the $C_{2+}$ composition sorbed by the second $C_2$ selective sorbent in sorption Zone A2 can be desorbed during an interval subsequent to the conversion reaction. Time intervals can be, independently, an interval ranging from 0.5 seconds to 15 seconds.

The invention is not limited to embodiments shown only in the FIGS. 1A and 2. For example, in other embodiments, the flow-through reactor can comprise a honeycomb monolith in the form of an elongated polygonal body. The honeycomb can comprise two or more portions, the portions being in side-to-side contact, with each section having one or more flow passages feeding into a flow passage in the adjacent portion. That is, the portions can be adjacent to each other, with each upstream of the mixing means or each downstream of the mixing means.

In other embodiments, the reactor stages can include three, four, five, six or more thermal masses, each thermal mass having one or more than one reaction zone and/or one or more than one $C_2$ selective sorbent zone. The reactor and/or $C_2$ selective sorbent zones in the reactor stages can be adjacent to each other or may optionally have a mixing means (e.g., mixing components or a gap) disposed between the portions.

As another example, the thermal mass or a portion of the thermal mass can comprise honeycomb monolith. Monoliths that have straight channels can be utilized to minimize pressure drop and enable greater reactor length. Preferred honeycomb monoliths can have channel densities that range from about 1 cell/cm$^2$ to 250 cells/cm$^2$.

Further, the thermal mass can include various bed packing, which may have different wetted areas. That is, the bed packing may include one or more of monoliths, pebble beds, tiles and/or combinations of different bed packings. For instance, a monolith can be disposed adjacent to a pebble bed and/or other particulate packing, which may have a different wetted area. In another embodiment, a foam monolith or packed bed can be utilized. These packings can be configured to provide a tortuous flow passage and have pore densities in the range of about 1 pore/cm to 20 pore/cm. In yet another embodiment, tiles may be utilized.

Example 3

Figure 3:
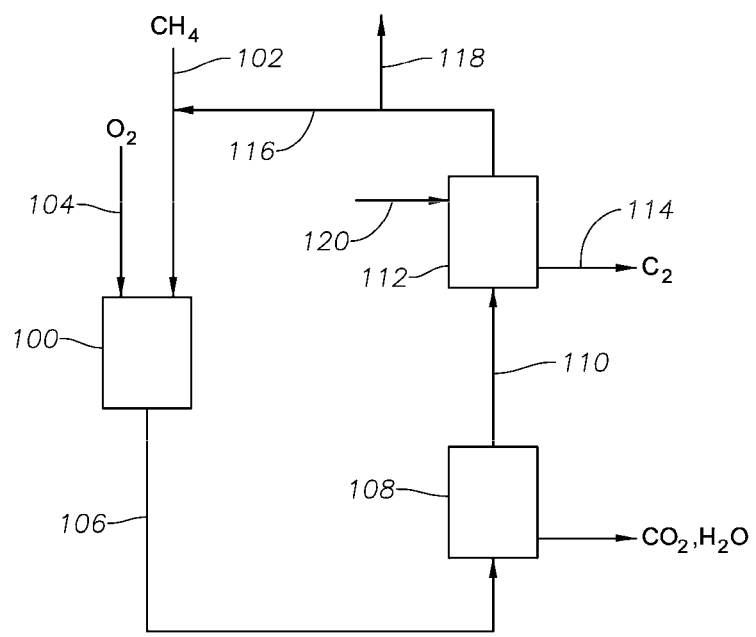
FIG. 3 is a simplified diagrammatic illustration of generalized aspects of the invention relating to a system for producing and selectively removing a $C_2$ composition.

With Reference to FIG. 3

A generalized system for producing and selectively removing a $C_2$ composition according to certain embodiments of the invention is depicted in FIG. 3. FIG. 3 illustrates a hydrocarbon conversion reactor 300, which can comprise: (i) a first region having a first thermal mass segment and a first aperture; (ii) a second region having a second thermal mass segment and a second aperture, and (iii) a catalytic conversion zone containing catalyst having an oxidative coupling functionality, oxydehydrogenation functionality or both, with the conversion zone further including an oxygen storage material. The catalyst and oxygen storage material are deposited with the first thermal mass segment and second thermal mass segment, as described in Example 1. The first and second regions are configured: 1) for flowing a first flow of an oxidant and a first flow of a hydrocarbon reactant to enter the reactor proximate to the first aperture, and 2) for flowing one or more components a reaction mixture to exit the reactor proximate to the second aperture.

A heating fluid comprising oxidant is flowed to the first aperture (not shown) of hydrocarbon conversion reactor 300 via a line 304 during a first time interval, with oxygen from the oxidant being stored with the oxygen storage material. After an appropriate time, flow of the oxidant is ceased. During a second time interval, hydrocarbon reactant containing methane ($CH_4$) flowed to the first aperture of the hydrocarbon conversion reactor 300 via the second aperture (not shown) and a line 302. At least a portion of the methane is catalytically converted to a reaction mixture comprised of $C_{2+}$ compositions, including at least ethane and ethylene, as well as $CO_2$ and water, and further includes any unreacted methane. The reaction mixture exits the reactor via a line 306 and is sent to a first separation unit 308 for removing at least a portion of the $CO_2$ and water. A $CO_2$ lean and water lean stream exits the first separation unit via a line 310 and is sent to a second selective sorption unit 312. $CO_2$ and water removed from the reaction mixture in the first separation unit 308 can conduct away. $CO_2$ is typically reacted in stage 308, and the products of the $CO_2$ reaction are conducted away (not shown).

At least a portion of the $C_2$ compositions (e.g., ethane, ethylene and/or acetylene) present in the $CO_2$ lean and water lean stream is selectively adsorbed by the second selective sorption unit 312, producing a methane rich stream 316. In addition, a purge stream 318 may be removed from unit 312. The methane rich stream is shown as being recycled via a line 316 back to the hydrocarbon conversion reactor 300 for re-processing, although at least a portion of the methane stream can be used for further processing in alternate processes. The adsorbed $C_2$ composition can be desorbed by lessening or discontinuing flow of the hydrocarbon reaction mixture through line 310 to the second selective sorption unit 312. Temperature and/or pressure of the second selection sorption unit 12 can be adjusted to desorb at least a portion of the sorbed $C_2$ composition, and the desorbed $C_2$ composition can be recovered by way of line 314. A sweep fluid can be flowed through a line 320 to the second selective sorption unit 312 to enhance desorption and recovery of the $C_2$ composition. Unreacted alkane can be recycled to the process via line 316. Should by-products such as CO accumulate in the recycle fluid, these can be periodically conducted away from the process via line 318.

Example 4

Figure 4:
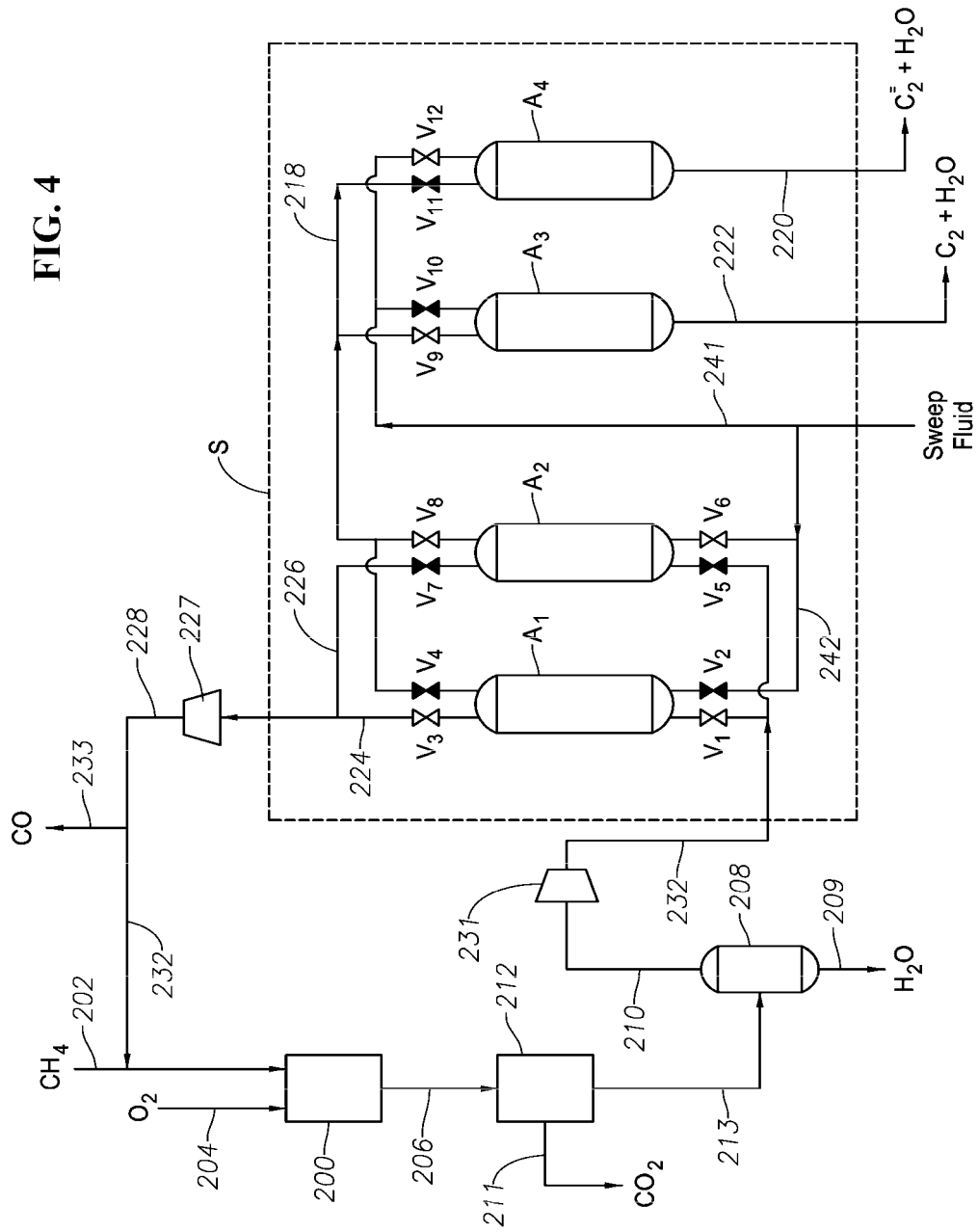
FIG. 4 is a simplified diagrammatic illustration of generalized aspects of the invention relating to another system for producing and selectively removing a $C_2$ composition.

With Reference to FIG. 4

An alternative embodiment of a system for selectively removing a $C_2$ composition according to certain embodiments of the present invention is depicted in FIG. 4. FIG. 4 illustrates a hydrocarbon conversion reactor 400, which is configured and operated as hydrocarbon conversion reactor 300 of FIG. 3. Specifically, a heating fluid comprising oxidant is flowed to the first aperture (not shown) of hydrocarbon conversion reactor 400 via a line 404 during a first time interval, with oxygen from the oxidant being stored with the oxygen storage material. After an appropriate time, flow of the oxidant is ceased. During a second time interval, hydrocarbon reactant containing methane ($CH_4$) flowed to the first aperture of the hydrocarbon conversion reactor 400 via the second aperture (not shown) and a line 402. At least a portion of the methane is catalytically converted to a reaction mixture comprised of $C_{2+}$ compositions, including at least ethane and ethylene, as well as $CO_2$ and water, and further includes any unreacted methane. The reaction mixture exits the reactor via a line 406 and is sent to a $CO_2$ separation unit 412 to selectively remove at least a portion of the $CO_2$ via a line 411, typically as a reacted product. A $CO_2$ lean stream exits the $CO_2$ separation unit via a line 413 and is sent to a water separation unit 408 to selectively remove at least a portion of the water via a line 409. A $CO_2$ lean and water lean stream exits the water separation unit 408 via a line 410 and is sent to an optional first compressor 431. The compressor can be used to boost the pressure of the $CO_2$ lean and water lean stream in line 410 to a pressure of ≥100 psig (489 kPag) if needed, with the pressurized $CO_2$ lean and water lean stream being passed by a line 432 to a $C_2$ selective sorption system S.

The $C_2$ selective sorption system S in FIG. 4 is a representative embodiment of a swing sorption system, comprising sorbent units A1-A4 containing $C_2$ selective sorbent for sorbing and recovering $C_2$ compositions. In the FIG. 4 embodiment, the sorbent units A1 and A3 are configured in adsorption mode, with valves V1, V3, V6, V8, V9 and V12 being in the open position. The sorbent units A2 and A4 are configured in desorption mode, with valves V2, V, 4, V5, V7, V10 and V11 being in the closed position. In this desorption mode, no fluid is flowed through lines 416 and 426. Flow through all other lines will be discussed as follows.

As shown in FIG. 4, the $CO_2$ lean and water lean stream is sent to sorbent unit A1, which is at a temperature lower than the hydrocarbon conversion reactor 400 and ≥50° C. As the stream passes through the sorbent unit A1, $C_2$ composition (e.g., ethane and ethylene) is adsorbed by the sorbent. Unreacted methane and other reaction components such as CO flow through the sorbent unit A1, exiting by way of open valve V3 and line 424 as a methane rich stream. In the mode of operation shown in FIG. 2, the methane rich stream is sent to a compressor 427, which may be optional. For example, only one of compressor 431 and compressor 427 may be utilized to maintain the desired operating pressures. However, both compressor 431 and compressor 427 can be utilized if desired.

The methane rich stream exits compressor 427 via line 428. In recycle mode, the methane rich stream can be recycled to hydrocarbon conversion reactor 400 via line 432. At times, the methane rich stream can build in CO content. In such case, the methane rich stream can be purged via a line 423 and further processed such as by flaring or recovery for use in a CO boiler.

In the FIG. 4 embodiment, desorption of the $C_2$ composition (e.g., ethane and ethylene) from the sorbent is being carried out in sorbent unit A2. Desorption is facilitated by increasing the temperature of the sorbent. In this example, sweep fluid (e.g., steam) is sent to sorbent unit A2 via a line 442 and open valve V6, with the sweep fluid being at a temperature greater than the temperature at which sorption of the $C_2$ composition in the sorbent unit A2 has been carried out. The heating of the sorbent by the sweep fluid and the movement of the sweep fluid through the sorbent unit A2 causes the $C_2$ composition to desorb from the sorbent. Then the desorbed $C_2$ composition and sweep fluid are passed through open valve V8 via a line 418 and passed through sorbent unit A3 via open valve V9.

In the FIG. 4 embodiment, the sorbent in the sorbent unit A3 is selective for sorbing ethylene from the $C_2$ composition, with the sorbent also being at a temperature lower than the hydrocarbon conversion reactor 400 and ≥50° C. Thus, as the $C_2$ composition and sweep fluid flow through the sorbent unit A3, the ethylene is selectively sorbed and the ethane and sweep fluid exit the sorbent unit A3 via a line 422. The sweep fluid can be relatively easily condensed at non-cryogenic temperatures and separated from the ethane to recover substantially pure ethane.

In the FIG. 4 embodiment, desorption of ethylene form the sorbent is being carried out in sorbent unit A4. Desorption is facilitated by increasing the temperature of the sorbent. In this example, sweep fluid (e.g., steam) is sent to sorbent unit A4 via a line 441 and open valve V12, with the sweep fluid being at a temperature greater than the temperature at which sorption of the ethylene from the $C_2$ composition has been previously carried out. The heating of the sorbent by the sweep fluid and the movement of the sweep fluid through the sorbent unit A4 causes the ethylene to desorb from the sorbent. Then the desorbed ethylene and sweep fluid exit the sorbent unit A4 via a line 420. The sweep fluid can be relatively easily condensed at non-cryogenic temperatures and separated from the ethylene to recover substantially pure ethylene.

While the present invention has been described and illustrated with respect to certain embodiments, it is to be understood that the invention is not limited to the particulars disclosed and extends to all equivalents within the scope of the claims. Unless otherwise stated, all percentages, parts, ratios, etc., are by weight. Unless otherwise stated, a reference to a compound or component includes the compound or component by itself as well as in combination with other elements, compounds, or components, such as mixtures of compounds. Further, when an amount, concentration, or other value or parameter is given as a list of upper preferable values and lower preferable values, this is to be understood as specifically disclosing all ranges formed from any pair of an upper preferred value and a lower preferred value, regardless of whether ranges are separately disclosed. All patents, test procedures, and other documents cited herein, including priority documents, are fully incorporated by reference to the extent such disclosure is not inconsistent and for all jurisdictions in which such incorporation is permitted.

The invention claimed is:

1. A process for producing a C2+ composition, comprising:
   (a) providing a reverse-flow reactor comprising (i) an oxidative coupling catalyst, (ii) and an oxygen storage material, and (iii) at least one thermal mass;
   (b) during a first time interval,
   i. passing a heating fluid comprising an oxidant and a hydrocarbon fuel through the reverse-flow reactor, wherein the oxidant is present in the heating fluid in a stoichiometric excess of that needed for substantially complete combustion with the hydrocarbon fuel,
   ii. exothermically combusting at least a first portion of the heating fluid's oxygen with the heating fluid's fuel to produce a heated combustion gas, storing at least a second portion of the heating fluid's oxidant with the oxygen storage material, and transferring heat from the heated combustion gas to the thermal mass, and
   iii. lessening or discontinuing the passing of the oxidant and fuel through the reverse-flow reactor; and
   (c) during a second time interval,
   i. passing a hydrocarbon reactant comprising methane through the reverse-flow reactor,
   ii. releasing at least a portion of the stored oxygen and reacting at least a portion of the released oxygen with at least a portion of the hydrocarbon reactant's methane in the presence of the oxidative coupling catalyst to produce a reaction mixture comprising a $C_{2+}$ composition which includes ethane and/or ethylene;
   (d) non-cryogenically separating from the $C_{2+}$ composition within the reverse-flow reactor at least a portion of the ethane and/or at least a portion of the ethylene, and conducting at least a portion of the separated ethane and/or at least a portion of the separated ethylene away from the reverse-flow reactor.

2. The process of claim 1, wherein the heat transfer is carried out during the storage of the oxygen with the oxygen storage material.

3. The process of claim 1, wherein the oxygen release during the second time interval is exothermic.

4. The process of claim 1, wherein the oxygen storage material comprises metal oxide.

5. The process of claim 4, wherein the metal oxide comprises perovskite.

6. The process of claim 1, wherein the hydrocarbon reactant comprises ≥90.0 wt. % of the methane, based on the weight of the hydrocarbon reactant.

7. The process of claim 1, wherein (i) the oxidant comprises molecular oxygen in air; (ii) the hydrocarbon reactant comprises ≥99.0 wt. % of the methane, based on the weight of the hydrocarbon reactant; and (iii) the reaction of step (c) (ii) is carried out at a methane:molecular oxygen molar ratio in the range of 10.0 to 20.0.

8. The process of claim 1, wherein, between the first time interval and the second time interval, a sweep fluid is passed through the reverse-flow reactor to remove at least a portion the combustion gas.

9. The process of claim 1, wherein:
   the thermal mass comprises first and second thermal mass segments, and during the second time interval, the first thermal mass segment is heated and the second thermal mass segment is cooled as the reaction of step (c) (ii) is continued.

10. The process of claim 9, wherein the reverse-flow reactor is an adiabatic reverse-flow reactor.

11. The process of claim 10, wherein (i) ≥50.0 wt. % of the first thermal mass segment, based on total weight of the first thermal mass segment, is located in a first region of the reverse-flow reactor, (ii) ≥50.0 wt. % of the second thermal mass segment, based on total weight of the second thermal mass segment, is located in a second region of the reverse-flow reactor, and (iii) ≥50.0 wt. % of the oxidative coupling catalyst, based on the weight of the oxidative coupling catalyst, is located in a third region of the reverse-flow reactor, the third region being located between the first and second regions.

12. The process of claim 10, wherein the process further comprises the steps of:
   (b1) during the first time interval,
   i. passing the heating fluid from the first thermal mass segment to the second thermal mass segment to heat the first thermal mass segment and the second thermal mass segment,
   ii. the storing of step (b) (ii) is carried out by storing at least the second portion of the oxidant with the oxygen storage material as the heating fluid is passed from the first thermal mass segment to the second thermal mass segment, and
   iii. lessening or discontinuing the passing of the heating fluid from the first thermal mass segment to the second thermal mass segment; and
   (c1) during the second time interval,
   i. passing the hydrocarbon reactant from the second thermal mass segment to the first thermal mass segment to contact the heated second thermal mass segment and heat the hydrocarbon reactant, and
   ii. the reacting of step (c) (ii) is carried out by contacting the heated hydrocarbon reactant with the oxidative coupling catalyst, in the presence of the stored oxidant, to catalytically convert at least a portion of the methane and produce the reaction mixture comprising the $C_{2+}$ composition.

* * * * *